US010765353B2

(12) United States Patent
Biederman et al.

(10) Patent No.: US 10,765,353 B2
(45) Date of Patent: Sep. 8, 2020

(54) CALIBRATION METHODS FOR A BANDAGE-TYPE ANALYTE SENSOR

(71) Applicant: Verily Life Sciences LLC, Mountain View, CA (US)

(72) Inventors: William James Biederman, Fox Island, WA (US); Brian Otis, Saratoga, CA (US); Jaclyn Leverett Wasson, Berkeley, CA (US); Zenghe Liu, Alameda, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 267 days.

(21) Appl. No.: 14/790,182

(22) Filed: Jul. 2, 2015

(65) Prior Publication Data
US 2017/0000390 A1 Jan. 5, 2017

(51) Int. Cl.
*A61B 5/05* (2006.01)
*A61B 5/1495* (2006.01)
(Continued)

(52) U.S. Cl.
CPC .......... *A61B 5/1495* (2013.01); *A61B 5/0002* (2013.01); *A61B 5/1473* (2013.01);
(Continued)

(58) Field of Classification Search
CPC ... A61B 5/1495; A61B 5/6848; A61B 5/7475; A61B 5/14514; A61B 5/6833;
(Continued)

(56) References Cited

U.S. PATENT DOCUMENTS

| 6,931,327 B2 * | 8/2005 | Goode, Jr. ........... A61B 5/0031 702/22 |
| 7,652,188 B2 | 1/2010 | Levanon et al. |

(Continued)

FOREIGN PATENT DOCUMENTS

| WO | 2013/028784 | 2/2013 |
| WO | 2015/017712 | 2/2015 |

OTHER PUBLICATIONS

International Search Report and Written Opinion of International Application No. PCT/US2016/039238 dated Sep. 16, 2016.
(Continued)

*Primary Examiner* — Navin Natnithithadha
*Assistant Examiner* — Andrey Shostak
(74) *Attorney, Agent, or Firm* — McDonnell Boehnen Hulbert & Berghoff LLP

(57) ABSTRACT

A flexible, body-mountable analyte sensing device includes a flexible substrate configured for mounting to skin of a living body. The sensing device additionally includes a sensor probe attached to the flexible substrate and configured to penetrate the skin such that a sensor disposed on the end of the sensor probe can be exposed to an analyte in interstitial fluid. The sensor could be an electrochemical sensor that includes two or more electrodes disposed at the end of the sensor probe and configured to electrochemically detect the analyte. The sensing device is configured to display detected concentrations or other information about the analyte in the interstitial fluid. The flexible substrate of the sensing device is configured to be adhered or otherwise mounted to the skin in a manner that minimally impacts activities of the living body.

19 Claims, 7 Drawing Sheets

(51) Int. Cl.
  *A61B 5/00* (2006.01)
  *A61B 5/145* (2006.01)
  *A61B 5/1473* (2006.01)

(52) U.S. Cl.
  CPC ...... *A61B 5/14514* (2013.01); *A61B 5/14532* (2013.01); *A61B 5/6801* (2013.01); *A61B 5/6833* (2013.01); *A61B 5/6848* (2013.01); *A61B 5/7225* (2013.01); *A61B 5/746* (2013.01); *A61B 5/7475* (2013.01); *A61B 2560/0238* (2013.01); *A61B 2560/0412* (2013.01); *A61B 2562/164* (2013.01)

(58) Field of Classification Search
  CPC .......... A61B 5/0002; A61B 2560/0238; A61B 2560/0412; A61B 2562/164; A61B 5/6801; A61B 5/1473; A61B 5/1486; A61B 5/746; A61B 5/7225; A61B 5/14532
  See application file for complete search history.

(56) References Cited

U.S. PATENT DOCUMENTS

| | | |
|---|---|---|
| 7,949,382 B2 | 5/2011 | Jina |
| 8,202,697 B2 | 6/2012 | Holmes |
| 8,326,652 B2 | 12/2012 | Sweeney |
| 8,385,998 B2 | 2/2013 | Zhang et al. |
| 8,512,245 B2 | 8/2013 | Markle et al. |
| 8,609,426 B2 | 12/2013 | Silver |
| 8,792,954 B2 | 7/2014 | Brister et al. |
| 8,956,289 B2 | 2/2015 | Kitajima et al. |
| 8,972,196 B2 | 3/2015 | Peyser et al. |
| 8,979,755 B2 * | 3/2015 | Szydlo-Moore ..... A61B 5/0002 600/301 |
| 2004/0204744 A1 * | 10/2004 | Penner ................. A61B 5/0031 607/23 |
| 2007/0073129 A1 * | 3/2007 | Shah ................... A61B 5/14532 600/365 |
| 2007/0100222 A1 | 5/2007 | Mastrototaro et al. |
| 2008/0033254 A1 * | 2/2008 | Kamath ............. A61B 5/14532 600/300 |
| 2008/0119707 A1 | 5/2008 | Stafford |
| 2008/0146871 A1 * | 6/2008 | Arneson ............... A61B 5/0002 600/101 |
| 2009/0294301 A1 | 12/2009 | Feldman et al. |
| 2010/0213080 A1 * | 8/2010 | Celentano ............ A61B 5/0002 205/777.5 |
| 2010/0213082 A1 | 8/2010 | Feldman et al. |
| 2011/0077490 A1 * | 3/2011 | Simpson ............ A61B 5/14532 600/345 |
| 2012/0296187 A1 | 11/2012 | Henning et al. |
| 2013/0041235 A1 | 2/2013 | Rogers et al. |
| 2013/0076531 A1 * | 3/2013 | San Vicente ......... A61B 5/0015 340/870.02 |
| 2014/0066888 A1 * | 3/2014 | Parikh ................. A61M 5/1723 604/504 |
| 2014/0180137 A1 | 6/2014 | Stivoric et al. |
| 2014/0275899 A1 | 9/2014 | Gottlieb et al. |
| 2014/0371553 A1 | 12/2014 | Winkelman |
| 2015/0005589 A1 | 1/2015 | Bly et al. |
| 2015/0018639 A1 | 1/2015 | Stafford |

OTHER PUBLICATIONS

Getting starting with Guardian REAL-Time Continuous Glucose Monitoring, product guide, 2009, Medtronic, Northridge, CA.
Guardian REAL-Time Continuous Glucose Monitoring System, User Guide, 2006, Medtronic MiniMed, Northridge, CA.
Dexcom G4 Platinum Professional Continuous Glucose Monitoring System, User's guide, 2014, Dexcom, IncG.
Dexcom G4 Platinum Continuous Glucose Monitoring System, Quick Start Guide, 2013, Dexcom, Inc., San Diego, CA.
Jonah Comstock, "Medtronic showcases smartphone-enabled continuous glucose monitoring," MobiHealthNews, http://mobihealthnews.com, Sep. 24, 2014.

* cited by examiner

CALIBRATION METHODS FOR A BANDAGE-TYPE ANALYTE SENSOR

BACKGROUND

Unless otherwise indicated herein, the materials described in this section are not prior art to the claims in this application and are not admitted to be prior art by inclusion in this section.

Certain medical conditions or states can be characterized by slow changes of a physiological property (e.g., a blood glucose concentration) over long periods of time and/or by infrequent, short-timescale events. Such physiological properties can be measured periodically (e.g., by periodically accessing blood of a person). Additionally or alternatively, an implanted or wearable device could be employed to provide continuous or near-continuous measurement of such physiological properties. Such implantable or wearable devices can be battery powered and/or powered by radio frequency energy or other wireless energy sources. Such implantable or wearable devices can be configured to operate at very low power levels to enable operation over extended periods of time, e.g., weeks, months, before exhausting a battery or other power source. Further, such devices can be configured to indicate measured physiological properties wirelessly (e.g., by using an RFID antenna and transmitter, by using a BLUETOOTH antenna and transmitter).

SUMMARY

Some embodiments of the present disclosure provide a body-mountable device that includes: (i) a flexible substrate that is configured to be mounted to a skin surface; (ii) a sensor configured to generate an electrical signal that is related to a physiological property; (iii) an analog-to-digital converter that is configured to receive the electrical signal generated by the sensor and to generate digital codes related to the received electrical signal, wherein the analog-to-digital converter is disposed on the flexible substrate; and (iv) a controller that is operably coupled to the analog-to-digital converter and that is disposed on the flexible substrate. The controller is configured to perform controller operations including: (a) obtaining calibration data; (b) operating the sensor to generate a plurality of samples of the electrical signal related to the physiological property; (c) operating the analog-to-digital converter to generate a plurality of digital codes corresponding to respective samples of the electrical signal generated by the sensor; (d) recording the generated plurality of digital codes; (e) determining that a trigger condition is met, and (f) determining, responsive to determining that the trigger condition is met, at least one value of the physiological property based on at least one recorded digital code and the calibration data.

Some embodiments of the present disclosure provide a body-mountable device that includes: (i) a flexible substrate that is configured to be mounted to a skin surface; (ii) a sensor configured to generate an electrical signal that is related to a physiological property; (iii) an analog-to-digital converter that is configured to receive the electrical signal generated by the sensor and to generate digital codes related to the received electrical signal and that is disposed on the flexible substrate; (iv) a communications interface that is disposed on the flexible substrate; and (v) a controller that is operably coupled to the analog-to-digital converter and that is disposed on the flexible substrate. The controller is configured to perform controller operations including: (a) operating the sensor, during a first period of time, to generate at least one sample of the electrical signal related to the physiological property; (b) operating the analog-to-digital converter, during the first period of time, to generate at least one digital code corresponding to the respective at least one sample of the electrical signal generated by the sensor; (c) transmitting, using the communications interface, an indication of the generated at least one digital code to an external system; (d) receiving, using the communications interface, information indicating a specified set of digital codes from the external system; (e) operating the sensor, during a second period of time, to generate a plurality of samples of the electrical signal related to the physiological property; (f) operating the analog-to-digital converter, during a second period of time, to generate a plurality of digital codes corresponding to respective samples of the electrical signal generated by the sensor; (g) determining whether each of the generated plurality of digital codes corresponds to a digital code of the specified set of digital codes; and (h) responsive to determining that a particular generated digital code corresponds to a digital code of the specified set of digital codes, providing an alert indication.

Some embodiments of the present disclosure provide a method that includes operating a body-mountable device, wherein the body-mountable device includes: (i) a flexible substrate that is configured to be mounted to a skin surface; (ii) a sensor configured to generate an electrical signal that is related to a physiological property; (iii) an analog-to-digital converter that is configured to receive the electrical signal generated by the sensor and to generate digital codes related to the received electrical signal and that is disposed on the flexible substrate; and (iv) a controller that is operably coupled to the analog-to-digital converter and that is disposed on the flexible substrate. Operating the body-mountable device includes: (a) obtaining, by the controller, calibration data; (b) generating, by the controller operating the sensor, a plurality of samples of the electrical signal related to the physiological property; (c) generating, by the controller operating the analog-to-digital converter, a plurality of digital codes corresponding to respective samples of the electrical signal generated using the sensor; (d) recording, by the controller, the generated plurality of digital codes; (e) determining, by the controller, that a trigger condition is met, and (f) determining, by the controller responsive to determining that the trigger condition is met, at least one value of the physiological property based on at least one recorded digital code and the calibration data.

These as well as other aspects, advantages, and alternatives, will become apparent to those of ordinary skill in the art by reading the following detailed description, with reference where appropriate to the accompanying drawings.

DETAILED DESCRIPTION

Figure 1:
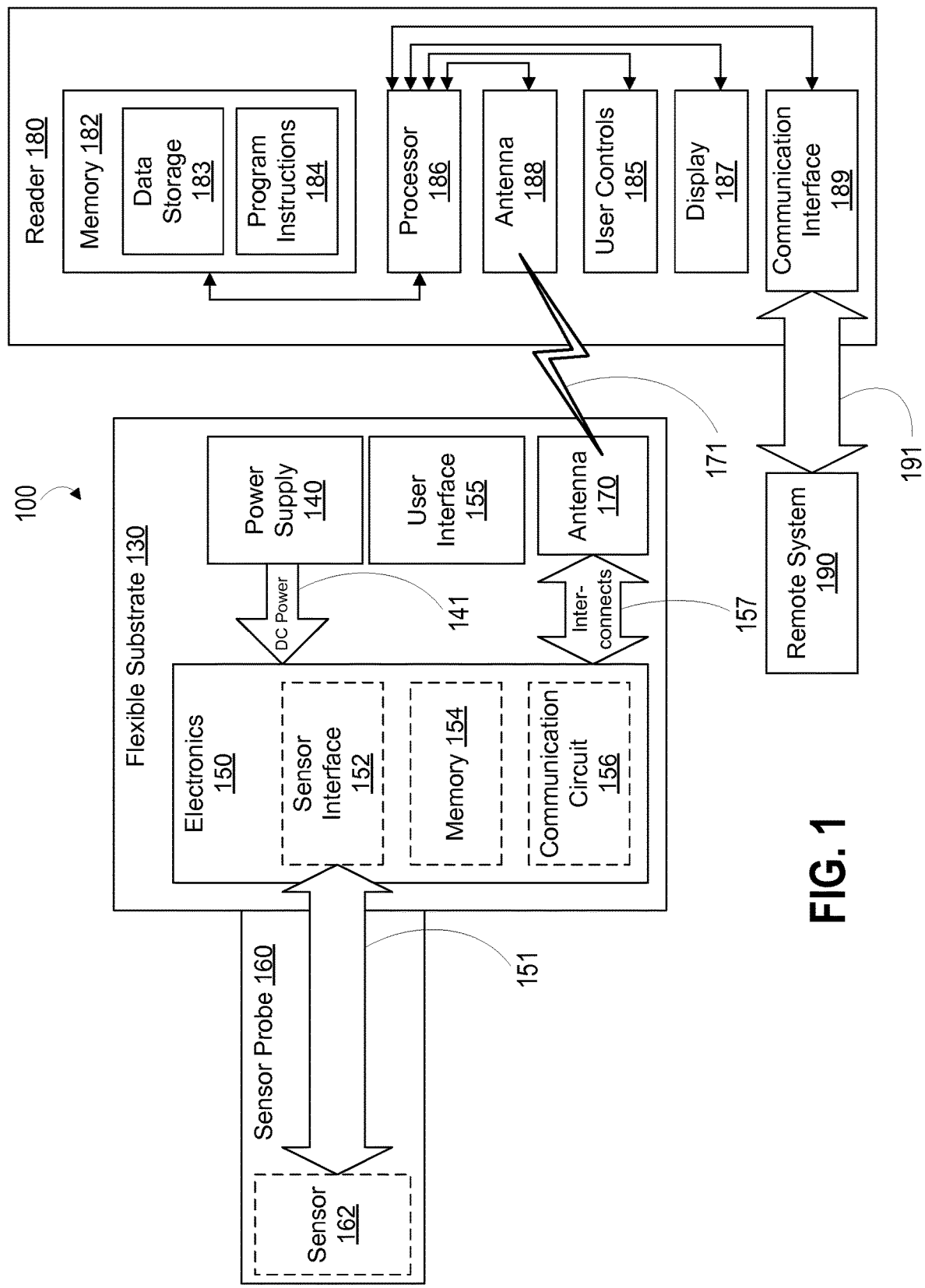
FIG. 1 is a block diagram of an example system that includes a body-mountable device in wireless communication with an external reader.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. OVERVIEW

Some embodiments of the present disclosure provide a body-mountable device having one or more sensors for quantitatively and qualitatively detecting one or more physiological properties (e.g., a heart rate, a temperature, a concentration of glucose or some other analyte in interstitial fluid or some other fluid) of a living body in real-time. Such a body-mountable device can be configured to operate using a very low amount of power, e.g., to allow the device to operate to measure a physiological property and to record and/or transmit information about the measured physiological property over a protracted period of time, e.g., many hours, days, or weeks. This could include operating the body-mountable device, to generate a plurality of digital codes (e.g., using an analog-to-digital converter (ADC) coupled to the output of a sensor configured to detect the physiological property) related to values of the physiological property of interest at respective different points in time (i.e., the generated codes represent samples of the physiological property over time) and to record the generated codes.

The body-mountable device could then operate, responsive to a trigger condition, to determine values of the physiological property over time based on the recorded digital codes and calibration data obtained by (e.g., manually input into, received wirelessly, programmed into during manufacture, determined by a controller of) the body-mountable device. The trigger condition could include receiving a request for one or more determined values of the physiological property (e.g., received from a user via a user interface, received from an external system via an antenna), receiving energy from a power source (e.g., radio frequency energy received wirelessly using an antenna of the body-mountable device), or according to some other factors or methods. Determining one or more values of the physiological property based on corresponding one or more recorded digital codes and calibration data obtained by the body-mountable device could include using logical gates, arithmetic logic units, hardware multipliers, or other electronic elements of the body-mountable device (e.g., of a controller of the body-mountable device) to add, subtract, multiply, divide, exponentiate, determine a logarithm, or to perform some other operations.

Such operation to determine values of a physiological property based on digital codes could require power and/or energy. Such operation could be performed in response to a trigger condition that includes the body-mountable device receiving a request for one or more values of the physiological condition. For example, a user could operate a user interface (e.g., a touch sensor, a button, a capacitive touchscreen) to request an indication of the value of the physiological property. The body-mountable device could determine that the trigger condition is met (e.g., that a user has input a request) and could responsively determine a value of the physiological property based on the most recently generated and recorded digital code and the calibration data. The body-mountable device could further provide an indication related to the determined value (e.g., could present a numerical indication of the determined value using a display of the user interface of the body-mountable device).

In another example, the body-mountable device could receive a request (e.g., by receiving information wirelessly using an antenna) for values of the physiological property from an external system. The body-mountable device could determine that the trigger condition is met (e.g., that an external system has transmitted a request) and could responsively determine one or more values of the physiological property based on corresponding one or more recorded digital codes and the calibration data. The body-mountable device could further transmit the determined values to the external system (e.g., wirelessly, using the antenna). Additionally or alternatively, the body-mountable device could transmit one or more of the recorded digital codes without converting them into determined values of the physiological property. In some examples, the trigger condition could include receiving sufficient radio frequency energy (e.g., using a loop antenna or otherwise configured antenna) to determine one or more values of the physiological property (e.g., to power a hardware multiplier, arithmetic logic unit, or other elements of the body-mountable device).

Body-mountable devices could be configured to be mounted to a skin surface of a living body (e.g., to skin of the upper arm or abdomen of a person). For example, the body-mountable device could include a flexible substrate on which components (e.g., electronics, a battery, an antenna, a user interface, one or more sensors) are disposed and that is configured to be mounted (e.g., using an adhesive) to the skin surface. The flexibility of the flexible substrate (and of the body-mountable device overall) could provide a sensing platform that minimally interferes with activities of a body to which the sensing platform is mounted and/or that can be mounted to a body comfortably for protracted periods of time. This could include the flexible substrate and/or the sensing platform being sufficiently flexible that the flexible substrate complies with the shape of the skin surface and deforms according to changes in the shape of the skin surface. Further, the sensor of such a body-mountable device could be disposed on a sensor probe configured to penetrate the skin such that the sensor is in contact with interstitial fluid (e.g., such that the sensor can detect a concentration, presence, or other properties of an analyte in interstitial fluid in the skin). Additionally or alternatively, one or more sensors of the device could be disposed on the flexible substrate.

The body-mountable device could include a variety of sensors configured to detect a variety of physiological properties and/or properties of the environment of the body-mountable device. In some examples, the sensor could include an analyte sensor configured to detect an analyte (e.g., glucose) in a fluid on or within the skin surface or other biological environment to which the sensing platform is mounted or exposed (e.g., interstitial fluid within or beneath the skin). In such examples, the sensor could include two or more electrodes configured to detect the analyte electrochemically (e.g., potentiometrically or amperometrically), a light sensor to detect the analyte optically (e.g., by illuminating and/or detecting light emitted from an analyte-sensitive substance that has an optical property related to the analyte), or by some other means.

Additionally or alternatively, the body-mountable device could include optical, electrical, thermal, mechanical, and/or other sensors (e.g., photoplethysmographic sensors, skin electrodes, tonometers, thermometers) configured to detect an optical or electrical property of a body, e.g., to detect a cardiovascular property (e.g., a pulse rate, a flow rate of blood in vasculature, an oxygen saturation of blood, an electrocardiogram signal), an electromyogram signal, a Galvanic skin response, a skin temperature, an ambient temperature, an atmospheric pressure, or some other physiological properties and/or properties of the environment of the body-mountable device. Such sensors could be configured to generate a voltage, a current, or some other electrical signal that has a property related to the physiological (or other) property of interest and that can be used, by an ADC, to generate a digital code related to the value of the physiological property.

Calibration data used to determine values of a physiological (or other) property based on digital codes could be related to a variety of properties of the body-mountable device (e.g., properties of the sensor, properties of the ADC) and/or of the environment of the body-mountable device (e.g., a relationship between a variable sensed by the sensor and the physiological property, a degree of perfusion of tissue proximate the sensor). In some examples, calibration data could include an offset and a gain to apply to generated digital codes to determine corresponding values of the physiological property (e.g., an amount to add or subtract from the digital code and/or a factor by which to multiply the digital code).

Calibration data could be obtained in a variety of ways, e.g., from an external system in communication with the body-mountable device, from input received from a user (e.g., using a user interface of the body-mountable device), from a device used manufacture and/or calibrate the body-mountable device during manufacture of the body-mountable device, or from some other external source. For example, calibration data could include and/or be determined from a value of the physiological property measured using some other system (e.g., a value of blood glucose measured using glucose meter and a lancet) and presented to the body-mountable device (e.g., via a wireless transmission from an external system, from an input presented by a user). Additionally or alternatively, the calibration data could be determined based on information generated by one or more sensors of the body-mountable device.

A body-mountable device can include a power source (e.g., a battery), electronics, an antenna, and/or other components. Such components could be disposed on a flexible substrate or some other elements configured to be mounted to skin of a living body or otherwise disposed proximate a body. The electronics can operate one or more sensors and/or ADCs to generate digital codes related to a physiological property of interest (e.g., related to the concentration of an analyte in interstitial fluid within or beneath the skin) and to record such generated digital codes for later use. The electronics could additionally operate the antenna to wirelessly communicate information (e.g., recorded digital codes, values of a physiological property determined therefrom) to an external reader or some other remote system via the antenna. One or more of the power source, antenna, electronics, or other components of the sensing platform could be flexible; for example, the power source could include a thin, flexible lithium ion battery. In some examples, one or more of the power source, antenna, electronics, or other components of the sensing platform could be sufficiently flexible to allow for flexibility of the overall sensing platform and/or of elements of the sensing platform that are able to be mounted to skin (e.g., to provide greater comfort and/or to minimize effect on user activities when mounted to skin of a user).

It should be understood that the above embodiments, and other embodiments described herein, are provided for explanatory purposes, and are not intended to be limiting. While embodiments of sensing platforms are described herein as being body-mountable and configured to detect properties (e.g., physiological properties) of bodies to which they are mounted, other embodiments are anticipated that are configured to be mounted to and/or disposed within or proximate to different environments and/or to detect different properties or variables. For example, a sensing platform configured to generate and record a plurality of digital codes related to a property of interest and to determine, responsive to determining that a trigger condition is met, values of the property of interest based on calibration data and on the generated digital codes could be configured to detect properties of a natural environment (e.g., properties of a fluid in a lake or stream, properties of the air), an artificial environment (e.g., properties of a fluid in a water treatment process, properties of the air in a building), a pharmaceutical or chemical synthesis environment, an animal body, or properties of or in some other environment of interest.

II. EXAMPLE ELECTRONICS OF A FLEXIBLE BIOSENSOR PLATFORM

FIG. 1 is a block diagram of a system that includes a body-mountable sensor platform 100 in wireless communication with an external reader 180. The body-mountable sensor platform 100 includes a flexible substrate 130 that is made of a flexible polymeric or metallic material formed to be mounted to a skin surface. The flexible substrate 130 provides a mounting surface for a power supply 140, electronics 150, user interface 155, and a communication antenna 170. The power supply 140 supplies operating voltages to the electronics 150 and/or other elements of the sensing platform 100. The antenna 170 is operated by the electronics 150 to communicate information to and/or from the body-mountable sensing platform 100. The antenna 170, the electronics 150, user interface 155, and the power supply 140 can all be situated on the flexible substrate 130.

The flexible substrate 130 can have a thickness, shape, composition, and/or other properties specified such that the flexible substrate 130 can be mounted to a skin surface of a living body and further such that such mounting minimally interferes with activities of the living body (e.g., motions of the living body). This could include the flexible substrate 130 being sufficiently flexible that mounting of the flexible substrate 130 to the skin surface causes a minimum of discomfort. The flexible substrate 130 could be composed of polyimide or some other flexible polymeric or other material. One or more surfaces of the flexible substrate 130 could be used as a platform for mounting components or elements of the antenna 170, the electronics 150, user interface 155, and the power supply 140 such as chips (e.g., via flip-chip mounting) and conductive materials (e.g., via deposition techniques) that form electrodes, antenna(e), and/or connections. The composition of the flexible substrate 130 could be specified such that metal contacts, traces, and interconnects can be patterned directly on the surface of the flexible substrate 130 (e.g., by sputtering, CVD, or some other deposition process) and/or on a coating or layer formed on one or more surfaces of the flexible substrate 130.

The electronics 150 disposed on the flexible substrate 130 could include a variety of devices. For example, the electronics 150 could include an antenna (e.g., a chip antenna), a microcontroller, amplifiers, light emitters, light detectors, analog-to-digital converters (ADCs), temperature sensors, transmitters, radios, transceivers, or some other component or components. Such components can be mounted to and/or electrically connected via interconnects or traces patterned on the flexible substrate 130. Further, antennas, electrodes, capacitors, resistors, or other components could be formed from such traces or other interconnects formed on the surface of the flexible substrate 130. The electronics 150 can include analog components (e.g., amplifiers, buffers, current sources), logic elements (e.g., comparators, counters, digital clocks or oscillators), or other components (e.g., ADCs) configured to operate the sensor 162 to detect an analyte or some other physiological property, an antenna (e.g., a loop, dipole, or other type of antenna formed on the flexible substrate 130, or a chip antenna disposed on the flexible substrate 130) to wirelessly indicate information (e.g., concentration levels, digital codes generated by an ADC) about the detected analyte or other physiological property, and/or to provide other functions.

Electrical interconnects (e.g., traces), antennas, and/or conductive electrodes (e.g., for an electrochemical analyte sensor, etc.) can be formed from conductive materials patterned on the flexible substrate 130 by a process for precisely patterning such materials, such as deposition, lithography, etc. The conductive materials patterned on the flexible substrate 130 can be, for example, gold, platinum, palladium, titanium, carbon, aluminum, copper, silver, silver-chloride, conductors formed from noble materials, metals, combinations of these, etc.

The body-mountable sensing platform 100 further includes a sensor probe 160 that is attached to the flexible substrate 130. The sensor probe 160 is an elongate element of the body-mountable sensing platform 100 that is configured to penetrate a skin surface such that a sensor 162 located at a distal end of the sensor probe 160 is in contact with a fluid (e.g., interstitial fluid or blood) containing an analyte of interest (e.g., glucose) when the sensor probe 160 is penetrating the skin. That is, the sensor probe 160 is configured to extend beneath the skin surface into an epidermal, dermal, or subcutaneous tissue of a body that includes the skin surface. The sensor probe 160 could be composed of a flexible material (e.g., polyimide) or a relatively inflexible material; further, a thickness, width, shape, or other properties of the sensor probe 160 could be specified to provide a degree of flexibility or inflexibility. In some examples, the sensor probe 160 could be formed from the same material as the flexible substrate 130; i.e., the sensor probe 160 could be an elongate portion of the flexible substrate 130 that extends from a portion of the flexible substrate 130 that is configured to be mounted to a skin surface and/or on which electronics 150 or other components are disposed. Alternatively, the sensor probe 160 could be attached to the flexible substrate 130. For example, the sensor probe 160 could include optical fiber(s), wire(s), elongate pieces of shaped silicon, patterned conductive traces, or other elements adhered, welded, bonded, or otherwise attached to the flexible substrate 130. Alternatively, such sensor probes could be used for other applications and/or in combination with components or devices other than a flexible substrate (e.g., 130) as described herein.

The substrate 130 includes one or more surfaces suitable for mounting the electronics 150 (including a sensor interface 152, a memory 154, and a communication circuit 156), the power supply 140, and the antenna 170. The flexible substrate 130 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. For example, the antenna 170 can be formed by depositing a pattern of gold or another conductive material on the flexible substrate 130. Similarly, interconnects 141, 151, 157 between the electronics 150 and the power supply 140, between the sensor interface 152 and the sensor 162, and between the communication circuit 156 and the antenna 170, respectively, can be formed by depositing suitable patterns of conductive materials on the substrate 130. A combination of microfabrication techniques including, without limitation, the use of photoresists, masks, deposition techniques and/or plating techniques can be employed to pattern materials on the substrate 130. The substrate 130 can be a material, such as polyimide, polyethylene terephthalate ("PET"), parylene, or another material sufficient to structurally support the circuitry and/or electronics.

The power supply 140 is configured to provide energy to power the electronics 150. For example, the power supply 140 could include a battery. Such a battery could be flexible, e.g., the battery could be a flexible lithium-ion battery or some other type of flexible battery. The battery could be flexible to allow the flexible substrate 130 to which the battery is mounted to flex in response to deformation and/or motion of a skin surface to which the flexible substrate 130 is mounted. Such flexibility could be provided to increase the comfort of a living body to which the sensing platform 100 is mounted and/or to minimally interfere with motions and/or activities of such a living body. A battery (or combination of batteries provided as part of the power supply 140) could have a capacity sufficient to power the device for a protracted period of time, e.g., 18 hours, a week, 14 days, or some other protracted period of time of periodic operation of the sensor 162, antenna 170, and memory 154 to detect an analyte or other physiological property, to record information related to the analyte or other physiological property in the memory 154, and to wirelessly communicate such detected information to the external reader 180. For example, the battery could be a flexible battery with a capacity of more than approximately 60 microamp-hours and a thickness of less than approximately 0.5 millimeters.

In some examples, the power supply 140 could include a rechargeable battery and could further include some means for recharging such a battery. For example, the power supply 140 could include contacts disposed on a surface of the flexible substrate 130 and configured to receive electrical power from complimentary contacts of a charging device (e.g., the external reader 180). In another example, the sensing platform 100 could include a loop antenna (e.g., a loop antenna comprising conductive traces patterned on the flexible substrate 130) and the power supply 140 could be configured to use the loop antenna to receive RF energy from an external device (e.g., the external reader 180); in some examples, such an RF-energy-receiving antenna could be the same antenna as the antenna 170 used to communicate with external devices.

The sensor interface module 152 and connection 151 between the sensor interface module 152 and sensor 162 could take a variety of forms according to the methods used to detect an analyte in fluid (e.g., interstitial fluid) to which the sensor 162 is exposed or to detect some other physiological property. The sensor 162 can include an analyte-selective substance that selectively interacts with the analyte in the fluid. The analyte-selective substance can include proteins, enzymes, reagents, ionophores, antibodies, fluorophores, nano-structured surfaces and/or structures, or other substances that selectively bind to, react with, change one or more properties in response to the presence of, or otherwise selectively interact with the analyte. The sensor 162 and sensor interface 152 can then detect the selective interaction between the analyte and the analyte-selective substance to detect a presence, concentration, or other properties of the analyte.

Such detection can include detecting the interaction between the analyte and the analyte-selective substance directly (e.g., by detecting a change in an optical property of the analyte-selective substance in response to interaction with the analyte, by detecting a change in electrical potentials at the sensor 162 due to accumulation of a charged analyte by the analyte-selective substance) or indirectly (e.g., by detecting a reaction product of the selective reaction of the analyte, e.g., by detecting hydrogen peroxide produced by oxidation of the analyte by the analyte-selective substance). Direct or indirect detection of the analyte could include electrochemical detection (i.e., the sensor could include two or more electrodes configured to electrochemically detect the analyte), optical detection (i.e., the sensor 162 and/or the sensor interface 152 could include a light emitter and/or light detector configured to detect an optical property of the analyte and/or the analyte-selective substance that is related to the presence, concentration, or some other property of the analyte), or some other detection means.

In some examples, the sensor 162 includes at least a reference electrode and a working electrode. The working electrode is selectively sensitive to an analyte of interest, for example, by having an analyte-selective substance localized proximate to the working electrode (e.g., by being disposed on a surface of the working electrode, by being disposed in an analyte-permeable polymer layer disposed on the working electrode). The sensor interface 152 is configured to operate the sensor 162 to electrochemically detect the analyte, e.g., to generate an electrical signal that is related to the analyte (e.g., a voltage, current, or other property of the generated signal is related to the concentration or other properties of the analyte).

In some examples, such an electrochemical analyte sensor 162 can be a potentiometric sensor. In such examples, a voltage can develop between the working and reference electrodes that is related to a concentration of analyte in a fluid to which the working electrode is exposed. Thus, the sensor interface 152 can measure a magnitude of the potentiometric voltage between the working electrode and the reference electrode to provide an indication of analyte concentration. For example, an analog-digital converter (ADC) of the sensor interface 152 could be operated to generate one or more digital codes related to the potentiometric voltage. In such embodiments, the sensor interface 152 can include a high-impedance voltmeter configured to measure the voltage difference between working and reference electrodes while substantially preventing the flow of current through the working and reference electrodes.

Additionally or alternatively, such an electrochemical analyte sensor 162 can be an amperometric sensor. In such examples, the sensor interface 152 can apply a specified voltage between the reference electrode and the working electrode. The applied voltage can drive an electrochemical current through the working electrode that is related to the concentration of an analyte near the working electrode. Such an electrochemical current can be related to redox or other reactions of the analyte at the surface of the working electrode and/or could be related to redox or other reactions of reaction products of the analyte at the surface of the working electrode (e.g., reaction products produced by reaction of the analyte due to selective interaction with the analyte-selective substance). Thus, the sensor interface 152 can measure a magnitude of the amperometric current passing through the working electrode to provide an indication of analyte concentration. For example, an ADC of the sensor interface 152 could be operated to generate one or more digital codes related to the amperometric current. In such embodiments, the sensor interface 152 can include a specified voltage source (to provide the specified voltage between the reference electrode and the working electrode) and a current meter configured to measure the current passing through the working electrode due to the applied specified voltage. In some examples, the sensor 162 could additionally include a counter electrode through which a return current (i.e. a current having a magnitude substantially equal but opposite to the current passing through the working electrode) could pass, such that substantially no current passes through the reference electrode. Such an embodiment could allow for the reference electrode to provide a more stable voltage relative to the fluid to which the sensor 162 is exposed.

In some examples, the sensor 162 could include an analyte-selective substance that has an optical property that is related to the presence, concentration, or some other property of the analyte. For example, the substance could include a fluorophore having a fluorescence intensity, a fluorescence lifetime, an emission wavelength, an excitation wavelength, or some other property that is related to the analyte. In some examples, such an analyte-selective substance could include a protein or other element configured to selectively bind to the analyte and to experience a conformation change in response to such binding. A fluorophore and a quencher could be attached to the protein such that the distance between the fluorophore and the quencher is related to whether the protein is bound to the analyte; as a result, the degree of fluorescence of the fluorophore could be related to whether the protein is bound to the analyte. Additionally or alternatively, a color, saturation, absorption spectrum, or some other optical property of a substance disposed at the end of the sensor probe could be related to the presence, concentration, or some other property of the analyte.

In such examples, the sensor interface 152 and/or the sensor 162 could include a light emitter and/or a light detector configured to illuminate and/or to receive light emitted from the analyte-sensitive substance, respectively, in order to determine the optical property of the substance that is related to the analyte. In some examples, the light emitter and/or light detector could be disposed as part of the sensor 162 (i.e., disposed on the sensor probe 160) and connected to the sensor interface 152 via conductive interconnects (e.g., the sensor interconnect 151 could include traces patterned or otherwise disposed on the sensor probe 160). Additionally or alternatively, the sensor probe 160 could include an optical fiber and the analyte-selective substance could be disposed on a distal end of such an optical fiber. In such examples, the light emitter and/or a light detector could be disposed at a proximal end of the optical fiber (e.g., on the flexible substrate 130 as part of the sensor interface 152), such that the light emitter and light detector illuminate and/or receive light from the analyte-sensitive substance via the optical fiber.

The sensor interface 152 includes an ADC configured to receive an electrical signal that is generated by the sensor 162 and/or elements of the sensor interface 152 that is related to a physiological property, e.g., to a body temperature, a blood flow rate, a blood oxygenation, a volume of blood in skin, a concentration or other properties of the analyte, or some other physiological property. The electrical signal could be a signal generated by an electrode, an amplifier, a buffer, a photodetector, a multiplexer, or some other electronic component(s) of the device 100. Further, a generated digital code could be related to a voltage, current, frequency, pulse rate, inter-pulse interval, or some other property of the electrical signal. The ADC could include a direct-conversion ADC, a successive approximation ADC, a ramp-compare ADC, a pipeline ADC, a sigma-delta ADC, or some other type of ADC and/or electronic components configured to generate digital codes based on properties of received electrical signals.

Digital codes generated by an ADC of the sensor interface 152 could each include a discrete number of binary digits (bits) according to an application. For example, an ADC of the sensor interface 152 could be configured to generate digital codes that are 8, 12, 16, or some other number of bits wide according to an application. The generated digital codes could have a specified relationship to the electrical signal received by the ADC and/or to the measured physiological property. For example, each digital code could correspond to a range of detected physiological property values and/or a range of values of the generated electrical signal, e.g., a digital code of "0010" could correspond to an electrical signal having a voltage between 2 millivolts and 3 millivolts, while a digital code of "0011" could correspond to an electrical signal having a voltage between 3 millivolts and 4 millivolts. The digital codes could be related to corresponding values of the electrical signal in order (e.g., a first digital code having a binary numerical representation that is greater than a binary numerical representation of a second digital code could correspond to a range of electrical signal values that are greater in magnitude than the range of values corresponding to the second digital code) or according to some other relationship. For example, such an ordering could be described by a linear or other relationship between the binary numerical representation of the digital codes and corresponding values of the electrical signal and/or the detected physiological property.

The electronics 150 could include means for determining values of a detected physiological property (e.g., analyte concentration) based on one or more digital codes generated by an ADC of the sensor interface 152. For example, the electronics 150 could include digital adders, multipliers, arithmetic logic units, programmable gate arrays, registers, accumulators, barrel shifters, or other logical elements configured to perform computations on generated digital codes in order to determine values of related physiological properties. In some examples, the operation of such elements could require significantly more power than operations to detect the physiological property and to generate related digital codes (e.g., to operate an electrochemical sensor to generate an electrical signal related to an analyte concentration, and to operate an ADC to generate a digital code based on such a generated electrical signal). For example, the device 100 could be configured to use less than approximately 1 microwatt of power to generate an electrical signal related to a physiological property and to generate digital codes based on such a generated electrical signal.

In such examples, the electronics 150 could operate at such a lower power level to generate and store a plurality of digital codes during a plurality of respective periods of time based on a measured physiological property (e.g., at a specified sampling rate, e.g., approximately once per second). The electronics 150 could then operate, at a higher power level, to determine one or more values of the physiological property at corresponding points in time based on corresponding one or more of the stored digital codes, e.g., by adding, subtracting, multiplying, or performing some other computations on the digital codes. Further, the electronics 150 could operate to indicate such determined values (e.g., using the user interface 155, using the communication circuit 156). Such operation (i.e., operating at a first, lower power level to generate and/or store a plurality of digital codes based on a physiological property, and intermittently operating at a higher power level to determine values of the physiological property and/or perform some other actions) of the device 100 could be performed to increase an duration of operation of the device 100 (e.g., to increase a number of digital codes related to a physiological property that could be generated and stored by the device 100) by reducing a power budget of the device 100.

The device 100 could be operated to determine one or more values of the physiological property (e.g., analyte concentration) based on one or more corresponding generated digital codes in response to a variety of trigger conditions or other considerations. For example, the device 100 could receive a user input (e.g., using the user interface 155) requesting a current or past value of the physiological property (e.g., a user could press a button of and/or contact the user interface 155) and the electronics 150 could responsively determine a value of the physiological property based on one or more corresponding digital codes (e.g., could determine a value of the physiological property based on the most recently generated digital code). Additionally or alternatively, the device 100 could receive a communication from another system (e.g., using the communication circuit 156) requesting a current or past value of the physiological property (e.g., a reader 180 could transmit a wireless signal 171 that indicates such a request) and the electronics 150 could responsively determine a value of the physiological property based on one or more corresponding digital codes.

In some examples, one or more values of the physiological property could be determined, based on corresponding generated digital codes, in response to the device 100 receiving additional power from an external source (e.g., power additional to the power provided by a battery of the power supply 140). For example, a battery of the power supply 140 could provide sufficient power to generate an electrical signal related to the physiological property (e.g., to operate the sensor 162 and/or sensor interface 152 to generate an electrical signal related to the concentration of an analyte in interstitial fluid within skin) and to generate and store a plurality of digital codes related to such an electrical signal (e.g., by operating an ADC of the sensor interface 152); however, the power provided by the battery could be insufficient to determine values of the physiological property based on such generated digital codes (e.g., could provide insufficient power to operate a hardware multiplier, arithmetic logic unit, or other logical and/or computational elements). The device 100 could be configured to receive power from an external source (e.g., RF energy received via, e.g., the antenna 170, solar energy, light energy, harvested thermal and/or mechanical energy from a body) and to determine one or more values of the physiological property based on corresponding generated digital codes when the received energy exceeds some threshold (e.g., the device 100 could determine whether a trigger condition that includes receiving energy above the threshold is met, and could further, responsive to determining that the trigger condition is met, determine one or more values of the physiological property).

The electronics 150 could be configured to perform some additional or alternative operations based on generated digital codes. For example, the electronics 150 could be configured to determine a health state or other information about a person based on the generated digital codes. In some examples, this could include determining corresponding values of the physiological property based on the digital codes, and further performing some determination based on the determined values of the physiological property (e.g., comparing the determined values to a specified range or threshold). Additionally or alternatively, a health state or other information about a person could be determined based on generated digital codes directly.

For example, a generated digital code could be compared (e.g., by logical elements of the electronics 150) to a specified set of digital codes (e.g., a set of specified digital codes that correspond to values of the physiological property that are indicative of a health state). Responsive to a determination that a generated digital code matched one of the specified set of digital codes, the electronics 150 could provide an indication (e.g., could indicate, via the user interface 155 and/or communication circuit 156, a health state corresponding to values of the physiological property that correspond to the set of digital codes) or could perform some other action(s). Such a specified set of digital codes could be provided by an external system (e.g., by an external reader 180 in response to receiving a digital code form the device 100 and receiving a measurement of the related physiological property from some other measurement system), could be determined by the device 100 (e.g., in response to a user inputting a known value of the related physiological property or some other information), or could be obtained by some other steps. Such operation and/or configuration of the device 100 could allow the device 100 to determine a health state or other information about a person while operating at a low power level (e.g., a power level less than a power level required to determine one or more values of a physiological property based on one or more generated digital codes).

The memory 154 could include a variety of volatile and nonvolatile electronic storage elements configured to provide means for the sensing platform 100 to record and/or log generated digital codes related to the physiological property (e.g., related to concentrations of an analyte), relative and/or absolute timings of the generation of such digital codes, calibration information, and/or other information detected by or input to (e.g., via user interface components 155 of the sensing platform 100) the sensing platform 100. For example, the memory 154 could include one or more EEPROM memories, flash memories, NVRAM memories, DRAM memories, SRAM memories, flip-flops, or other information storage elements. The memory 154 could have an information storage capacity sufficient to record some specified period of generated digital codes at some specified rate of detection; e.g., the memory 154 could have a capacity sufficient to record more than 18 hours, a week, or some other protracted period of time of detected information (e.g., physiological properties, analyte concentrations) when detected at a rate of approximately once per minute. Additionally or alternatively, the sensing platform 100 could be in communication with a memory that is external to the sensing platform 100 and that could be used as described above (e.g., to store generated digital codes, to store and/or access calibration or other configuration data of the sensing platform 100).

The user interface 155 is configured to receive inputs from a user (e.g., a user to whose body the device is mounted) and/or present outputs to the user to provide some application(s) of the sensing platform 100. Such user-interface elements (e.g., displays, sensors, buttons) could be flexible and/or mounted to the flexible substrate 130 of the sensing platform 100. In some examples, the user interface 155 could provide means for changing or setting an operational state of the sensing platform 100 and/or for causing the performance of some function by the sensing platform 100. For example, the user interface 155 could provide means for a user to cause the sensing platform 100 to perform a measurement of the physiological property using the sensor 162 (i.e., to generate an electrical signal related to the physiological property, to generate a digital code based on the electrical signal, and/or to determine a value of the physiological property based on the generated digital code), to set the sensing platform 100 into a sleep or other low-power state, to set a rate of operation of the sensor 162 to detect the physiological property, or to control some other aspect of operation or function of the sensing platform 100. In some examples, the user interface 155 could provide means for inputting calibration or other data to the sensing platform 100, e.g., for inputting calibration data related to the operation of the sensor 162 to detect the physiological property. Additionally or alternatively, the user interface 155 could provide means for inputting information about the state of a user of the sensing platform 100, e.g., to indicate a physical or mental state of the user, to indicate an activity of the user, to indicate that the user has eaten a meal or taken a drug, or to indicate some other information. The user interface 155 could provide means for indicating information to a user, for example, information about the operation of the sensing platform 155 (e.g., battery charge state, an amount of free memory), determined physiological properties (e.g., a blood glucose level detected using the sensor 162), or some other information available to the sensing platform 100.

The user interface 155 could be configured to detect a variety of inputs. The user interface 155 could be configured to detect sound (e.g., voice commands), motions of the sensing platform 100 (e.g., a gesture that includes motion of the skin surface to which the sensing platform is mounts), contact between the sensing platform 100 and a finger or other portion of a user's body, or some other inputs. For example, the user interface 155 could be configured to detect a location, motion, pressure, gesture, or other information about objects (e.g., a finger or other body part) near the sensing platform 100. The user interface 155 could include a capacitive touch sensor configured to detect a single touch, multiple touches, gestures, swipes, or other inputs. The user interface 155 could include flexible components. In some examples, the user interface 155 could include one or more elements in common with the sensor 162. For example, the sensor 162 of the sensing platform 100 could be configured to detect a temperature of the skin surface to which the sensing platform 100 is mounted; additionally, the sensor 162 could be used to detect inputs (e.g., contact between the sensing platform 100 and a finger or other object) by detecting changes over time in the temperature detected using the sensor 162.

The user interface 155 could be configured to provide a variety of different types of information via a variety of means. The user interface 155 could indicate information related to the operational state of the sensing platform 100 (e.g., to indicate a battery charge state or free memory space of the device) and/or related to the physiological property detected using the sensor 162 (e.g., to indicate a blood glucose level detected using the sensor 162). The user interface 155 could be used to indicate a course of action that a user could take (e.g., to administer a drug, to seek medical assistance). The user interface 155 could be used to indicate some alert generated by the sensing platform 100 (e.g., an alert that a determined value of the physiological property is outside of specified limits, an alert that a generated digital code matches one of a specified set of digital codes, an alert that a user is experiencing an adverse health state). The user interface 155 could include light-emitting elements (e.g., LEDs, OLEDs, displays), color-changing elements (e.g., e-ink elements or displays, LCDs), haptic elements (e.g., vibrators, buzzers, electrohaptic elements), acoustical elements (e.g., buzzers, speakers), or some other elements configured to indicate some information, e.g., to a user. The user interface 155 could include flexible elements, e.g., the user interface 155 could include a flexible OLED display.

The electronics 150 include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the body-mountable sensing platform 100 is configured to indicate information (e.g., generated digital codes, values of the physiological property determined therefrom) by modulating an impedance of the antenna 170 in a manner that is perceivably by the external reader 180. For example, the communication circuit 156 can cause variations in the amplitude, phase, and/or frequency of backscatter radiation from the antenna 170, and such variations can be detected by the reader 180. Such wireless communication could be compatible with one or more existing backscatter wireless communications standards, e.g., RFID. Additionally or alternatively, the communication circuit 156 and antenna 170 could be configured to transmit wireless signals according to some other method, e.g., according to the BLUETOOTH (e.g., BLUETOOTH Low Energy), ZIGBEE, WIFI, LTE, and/or some other wireless communications standard or scheme. In some examples, such communications (e.g., data transmitted from the sensor platform 100, operational instructions transmitted to the sensor platform 100) could be cryptographically secured; that is, the wireless communications link could be encrypted.

The sensor interface 152 is connected to the sensor 162 via a sensor interconnect 151. In some examples, the sensor interconnect 151 could include a patterned conductive material (e.g., gold, platinum, palladium, titanium, copper, aluminum, silver, metals, combinations of these, etc.) to connect electrodes, light emitters, light detectors, or other components of the sensor 162 to a terminal on a or other component(s) comprising the sensor interface 152. Similarly, the electronics 150 are connected to the antenna 170 via interconnects 157. Additionally or alternatively, the sensor interconnect 151 could include an optical fiber or other means for transmitting light between the sensor 162 and the sensor interface 152. For example, the sensor interface 152 could comprise a light emitter and/or light detector and the sensor 162 could include an analyte-sensitive substance that has an optical property that is related to the presence, concentration, or some other property of the analyte. In such examples, the light emitter and/or a light detector could be disposed at a proximal end of the optical fiber, such that the light emitter and light detector illuminate and receive light from the analyte-sensitive substance via the optical fiber of the sensor interconnect 151. Other configurations of the sensor interconnect 151 are anticipated (e.g., capillary tubes, microfluidic elements, etc.).

It is noted that the block diagram shown in FIG. 1 is described in connection with functional modules for convenience in description. However, embodiments of the body-mountable sensing platform 100 can be arranged with one or more of the functional modules ("sub-systems") implemented in a single chip, integrated circuit, and/or physical feature or on multiple such elements.

The external reader 180 includes an antenna 188 (or group of more than one antenna) to send and receive wireless signals 171 to and from the body-mountable sensing platform 100. The external reader 180 also includes a computing system with a processor 186 in communication with a memory 182. The external reader 180 can also include one or more of user controls 185, a display 187, and a communication interface 189. The memory 182 is a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., generated digital codes and/or values of the physiological property determined therefrom that are related to electrical signals generated using the sensor 162), program settings (e.g., to adjust behavior of the body-mountable sensing platform 100 and/or external reader 180), etc. The memory 182 can also include program instructions 184 for execution by the processor 186 to cause the external reader 180 to perform processes specified by the instructions 184. For example, the program instructions 184 can cause external reader 180 to perform any of the function described herein. For example, program instructions 184 may cause the external reader 180 to provide a user interface that allows for retrieving information communicated from the body-mountable sensing platform 100 (e.g., digital codes generated by the sensor interface 152, values of the physiological property determined therefrom) by displaying that information on the display 187 in response to commands input through the user controls 185. The external reader 180 can also include one or more hardware components for operating the antenna 188 to send and receive the wireless signals 171 to and from the body-mountable sensing platform 100. For example, oscillators, frequency injectors, encoders, decoders, amplifiers, filters, etc. can drive the antenna 188 according to instructions from the processor 186.

The external reader 180 can also be configured to include a communication interface 189 to communicate signals via a communication medium 191 to and from a remote system 190. For example, the remote system 190 may be a smart phone, tablet computer, laptop computer, or personal computer, and communication interface 189 and communication medium 191 may be a BLUETOOTH module and wireless BLUETOOTH communication signals, respectively. In this example, the external reader 180 may be configured to send information about the physiological property detected by the sensing platform 100 to the smart phone, tablet computer, laptop computer, or personal computer for storage and offline analysis. In another example, the remote system 190 is a server at a clinic or physician's office, the communication interface 189 is a WIFI radio module, and the communication medium 191 is elements of the internet sufficient to enable the transfer of data between the remote server and the WIFI radio module. A physician may use this data to make determinations or diagnoses related to the subject's condition. Further, the external reader 180 may be configured to receive signals from a remote server, such as instructions sent by a physician at a remote location to, for example, increase or decrease sampling frequency. Communication interface 189 could be configured to enable other forms of wired or wireless communication; for example, CDMA, EVDO, GSM/GPRS, WIMAX, LTE, infrared, ZIGBEE, ETHERNET, USB, FIREWIRE, a wired serial link, or near field communication.

The external reader 180 can be a smart phone, digital assistant, or other portable computing device with wireless connectivity sufficient to provide the wireless communication link 171. The external reader 180 can also be implemented as an antenna module that can be plugged in to a portable computing device, such as in an example where the communication link 171 operates at carrier frequencies not commonly employed in portable computing devices. In some instances, the external reader 180 is a special-purpose device configured to be periodically placed relatively near the sensing platform 100 to allow the wireless communication link 171 to operate with a low power budget.

In some examples, the sensing platform 100 could be configured to detect glucose in the body of a person and the external reader 180 could include or be in contact with an insulin pump. Such an insulin pump could include a supply of insulin and a pump configured to provide the insulin, at a controlled rate, into the body of the person (e.g., through a tube placed in and/or through the skin of the body of the person using, e.g., a needle). In such examples, the insulin pump could be operated based on measurements of glucose levels (e.g., concentrations, digital codes) in the body of the person detected using the sensor 162. For example, the insulin pump could be operated to provide insulin at a rate based on the detected glucose levels such that the blood glucose levels of the person are maintained within a specified range, or according to some other scheme (e.g., the insulin pump could be operated as part of a feedback loop that includes the sensor 162). Additionally or alternatively, the external reader 180 could include or be in contact with a pump for some other pharmaceutical and could be operated to provide that pharmaceutical at a controlled rate based on a detected level of glucose or of some other physiological property detected using the sensor 162.

In an example where the body-mountable sensing platform 100 has been mounted to skin of a living body such that the sensor 162 is in contact with interstitial fluid of the living body, the sensing platform 100 can be operated to detect the physiological property of (e.g., to measure a concentration of the analyte in) the interstitial fluid. The interstitial fluid is an extravascular fluid that suffuses many of the tissues of a living animal body. The interstitial fluid is continuously replenished by the blood supply through capillaries in the structure of tissue (e.g., dermal tissue, subcutaneous tissue) and includes many biomarkers found in blood that are analyzed to characterize a person's health condition(s). For example, the interstitial fluid includes urea, glucose, calcium, sodium, cholesterol, potassium, phosphate, other biomarkers, etc. The biomarker concentrations in the interstitial can be systematically related to the corresponding concentrations of the biomarkers in the blood, and a relationship between the two concentration levels can be established to map interstitial fluid biomarker concentration values to blood concentration levels. Thus, measuring interstitial fluid analyte concentration levels using sensing platforms as described herein can provide a technique for monitoring analyte levels in comparison to blood sampling techniques performed by lancing a volume of blood to be analyzed outside a person's body. Moreover, the body-mountable sensor platform disclosed here can be operated substantially continuously to enable real time measurement of analyte concentrations or other information about an analyte or other physiological property.

In some embodiments, the body-mountable sensing platform 100 can operate to non-continuously ("intermittently") indicate information related to a detected physiological property (e.g., concentration values of an analyte). For example, the body-mountable sensing platform 100 could operate to periodically operate the sensor 162 to generate and store digital codes related to the physiological property in the memory 154. The sensing platform 100 could then less frequently operate to transmit stored information relating to more than one detection of the analyte, e.g., in response to determining that a trigger condition is met. Such a trigger condition could include a user could operating the external reader 180 to request such information transmission by the sensing platform 100. In another example, the sensing platform 100 could indicate to a user (e.g., via a light, vibration motor, or other user interface element(s) of the sensing platform) that the user should operate the external reader 180 to receive such transmitted information from the sensing platform (e.g., due to the memory 154 being nearly full, due to a battery of the power supply 140 being nearly depleted). Other operations of the systems shown to continuously, periodically, and/or intermittently use the sensor 162 and sensor interface 152 to generate digital codes related to a physiological property, use the memory 154 to store the generated digital codes, and/or use the antenna 170 to wirelessly indicate such digital codes and/or values of the physiological property determined therefrom are anticipated.

Devices as described herein (e.g., 100) could generate and store digital codes related to physiological properties (e.g., to concentrations of an analyte) in a variety of different ways. For example, such devices could generate and record a plurality of such digital codes in a specified order (e.g., sequentially) in a memory. In some examples, a difference between subsequent generated digital codes could be recorded in the memory (e.g., to increase a resolution of values of the physiological property determined therefrom). In some examples, a relative or absolute timing of the generated digital codes could also be stored in the memory (e.g., to allow a comparison of the generated codes to the timing of known events or other information, to allow multiple sets of stored calibration data to be used to determine values of the physiological property based on the digital codes and on the relative timing of the digital codes and times corresponding to the multiple sets of stored calibration data).

Figure 2:
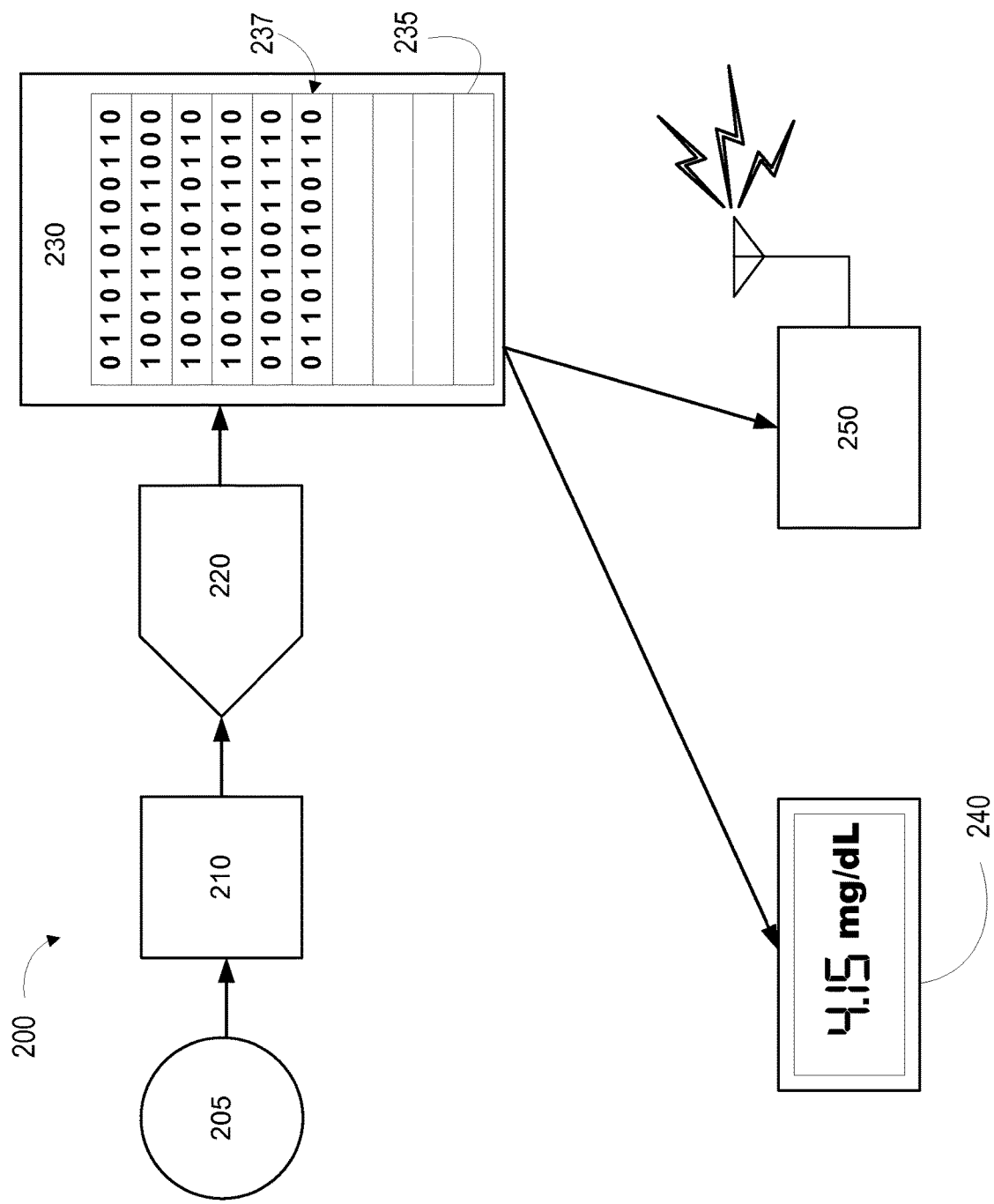
FIG. 2 is a block diagram of an example system that includes an analog-to-digital converter configured to generate digital codes related to an electrical signal generated by the system.

As an illustrative example, FIG. 2 shows a system 200 configured to generate a plurality of digital codes related to a physiological property, to determine one or more values of the digital property based on corresponding digital codes (e.g., responsive to a trigger condition being met), and to indicate such determined values (e.g., to a user, to a remote system). The system 200 includes a sensor 205 (e.g., an electrochemical sensor, a light sensor and an optical substance configured to have an optical property related to the physiological property) and a signal conditioner 210 (e.g., an amplifier, a buffer, a potentiostat, a transimpedance amplifier, and/or some other electronic components) configured to generate an electrical signal related to the physiological property (e.g., having a voltage, current, frequency, duty cycle, or other properties related to the physiological property). The system further includes an analog-to-digital converter (ADC) 220 configured to generate digital codes based on the generated electrical signal.

The system further includes a controller 230 (e.g., a microcontroller, one or more integrated circuits) configured to receive the digital codes from the ADC 220 and to perform some operations based on the received digital codes. The controller 230 includes a memory 235 that can be used to store the received digital codes (a plurality of stored digital codes are indicated by the binary codes illustrated in the Figure; the most recently generated digital code 237 is indicated by the arrow). The controller could also be configured to operate the sensor 205, signal conditioner 210, and/or ADC 220 to generate the digital codes. The system includes a user interface 240 configured to indicate (e.g., display) determined values of the physiological property (or other information) to a user and/or to receive inputs from a user. The system additionally includes a communication interface 250 configured to indicate determined values of the physiological property (or other information) to an external system and/or to receive information from an external system.

As shown in FIG. 2, the memory 235 is configured to store a plurality of 12-bit digital codes related to a physiological property of interest. The order of the stored codes in the memory could be related to the order in which the digital codes were generated, e.g., the indicated digital code 237 could be the most recently generated digital code. Alternatively, a description of the relative ordering of the generated digital codes and/or the location of such codes within the memory 235 could be specified according to some other arrangement and/or information describing such an ordering could be stored (e.g., in the memory 235). In some examples, the timing of the generated digital codes could also be stored in the memory 235 and the order of the stored codes within the memory 235 could be random or according to some other arrangement. Note that the last cells of the memory 235, as illustrated, are blank. In practice, such cells could be all zeros, all ones, some other specified pattern, or could contain random contents according to the configuration of the memory 235 and/or the controller 230. In some examples, the cells could contain generated digital codes related to the physiological property. For examples, the controller 230 could operate the memory 235 as a ring buffer, over-writing the least recently generated stored digital codes with newly generated digital codes. In some examples, the order of generation of the stored digital codes could be unrelated to the order of corresponding cells of the memory, e.g., The generated digital codes could be related in a variety of ways to the generated electrical signal that is related to the physiological property of interest (e.g., an analyte concentration). For example, each digital code could correspond to a range of values of the generated electrical signal, e.g., a digital code of "0010" could correspond to an electrical signal having a voltage between 2 millivolts and 3 millivolts, while a digital code of "0011" could correspond to an electrical signal having a voltage between 3 millivolts and 4 millivolts. The digital codes could be related to corresponding values of the electrical signal in order (e.g., a first digital code having a binary numerical representation that is greater than a binary numerical representation of a second digital code could correspond to a range of electrical signal values that are greater in magnitude than the range of values corresponding to the second digital code) or according to some other relationship. For example, such an ordering could be described by a linear or other relationship between the binary numerical representation of the digital codes and corresponding values of the electrical signal and/or the detected physiological property. In some examples, each digital code could be related to a sigma-delta modulated, pulse-code modulated, or otherwise altered version of the electrical signal. Additionally or alternatively, each generated digital code could be related to a change in the generated electrical signal, e.g., to provide for a higher-resolution record of the physiological property.

Note that FIG. 2 illustrates the memory 235 as part of the controller 230 as a non-limiting illustrative example. A memory configured to store or record digital codes as described herein could be separate from and electrically coupled to a controller, could be composed of multiple components, or could be otherwise alternatively configured. In some examples, such a memory could be removable, e.g., could be part of an SD card, USB memory stick, or could include some other form of removable media.

The controller 230 can be configured to perform a variety of operations, e.g., operations related to one or more generated and/or stored digital codes related to a detected physiological property. The controller 230 is configured to determine values of the physiological property (e.g., concentration values of an analyte, values of the relative or absolute volume of blood in a portion of subsurface vasculature, values of the magnitude of a biopotentials) based on one or more generated digital codes. The controller 230 is further configured to indicate such determined physiological property values, e.g., to indicate determined values to a user using a display of the user interface 240 and/or to wirelessly indicate such values to an external system using the communication interface 250.

Determination of a value of the physiological parameter based on a generated digital code (e.g., by operating an arithmetic logic unit, hardware multiplier, or some other electronic elements) could require the use of a specified amount of power. The controller 230 could be configured to intermittently perform such determinations, e.g., to increase a period of time during which the system 200 could operate while powered by a battery. For example, the controller 230 could operate to generate a plurality of digital codes related to the physiological property (e.g., using the sensor 205, signal conditioner 210, and ADC 220). The controller 230 could then operate to determine one or more values of the physiological parameter based on corresponding generated and stored digital codes. Determination of the value(s) of the physiological property could be performed in response to some factor or determination, e.g., in response to determining that a trigger condition is met. Such a trigger condition could include receiving a request for such information (e.g., via the user interface 240 and/or communication interface 250), receiving a supplementary source of power (e.g., RF power transmitted from an external system, solar power from ambient light, thermal or mechanical power harvested from a body to which the system 200 is mounted), or some other events, inputs, or conditions.

Operation of the controller 230 to determine values of the physiological property in response to requests, when additional power is available, or according to other trigger conditions could allow the system 200 to operate for an extended period of time (e.g., to record information related to the physiological property at a plurality of points in time, corresponding to a plurality of generated and/or stored digital codes) relative to operation that includes determining a value of the physiological property when each related digital code is generated. For example, a sensing platform configured and/or operated in such a manner could operate, powered by a low-capacity battery, to generate and/or store digital codes related to a physiological property of interest for a period of many days, e.g., more than approximately 2 weeks. Further, such operation to generate and record digital codes related outputs generated by a sensor, as described above, could use less than approximately 1 microwatt of power.

The controller 230 can be configured to determine values of the physiological property based on generated digital codes using calibration data. Such calibration data could include information describing a relationship between the digital codes and the physiological property, e.g., could describe a calibration curve relating binary values of the digital codes to values (e.g., concentrations) of the physiological property. For example, such calibration data could include offset values that could be digitally added or subtracted from the digital codes, gain values that could be used to scale digital codes, or other information. In some examples, calibration data could include lookup tables or other information describing, for one or more particular digital codes, corresponding values of the physiological property.

In some examples, the controller 230 could determine a physiological property value, based on a particular generated digital code, using more than one set of calibration data. For example, multiple set of calibration data could be related to multiple corresponding points in time (e.g., could be determined based on values of the physiological property detected by some other system at the multiple points in time). A relative timing between the multiple points in time corresponding to the sets of calibration data and a timing of the particular generated digital code could be used to determine a value of the physiological property, e.g., by determining a combination of the sets of calibration data based on the relative timings (e.g., a weighted average), by determining multiple values of the physiological property based on the particular generated digital code and combining them based on the relative timings (e.g., a weighted average of the determined values), or according to some other method. In some examples, the multiple points in time corresponding to the multiple sets of calibration data could be earlier points in time than the timing of the particular generated digital code.

The controller 230 could receive such calibration data from a user (e.g., by the user inputting such data using the user interface 240) and/or from an external system (e.g., by receiving such information via the communications interface 250). For example, the controller 230 could receive offset values, gain values, lookup tables, or other information in such a way. Additionally or alternatively, the controller 230 could determine such calibration data. In some examples, the controller 230 could receive a measured value of the physiological property from an external system (e.g., from an external device configured to detect the physiological property, from a user operating the user interface 240) and could determine calibration data (e.g., a gain value that could subsequently be used by the controller 230 to determine a value of the physiological property based on generated digital codes) based on the received physiological property value and one or more digital codes generated by the ADC 220.

In some examples, the controller 230 could present a determined value of the physiological property to a user using the user interface 240 and the user could provide inputs to indicate whether the determined value is greater than or less than a known correct value of the physiological property (e.g., a value provided by some other system configured to detect the physiological property). Such inputs could be used to update the calibration data (e.g., to increase or decrease a gain value); the controller 230 could then use the updated calibration data to determine a new value of the physiological property based on the generated digital code. The user could again use the user interface 240 to indicate any difference between the newly determined value and the known correct value. In this way, the controller 230 could iteratively determine calibration data based on inputs from the user.

Figure 3:
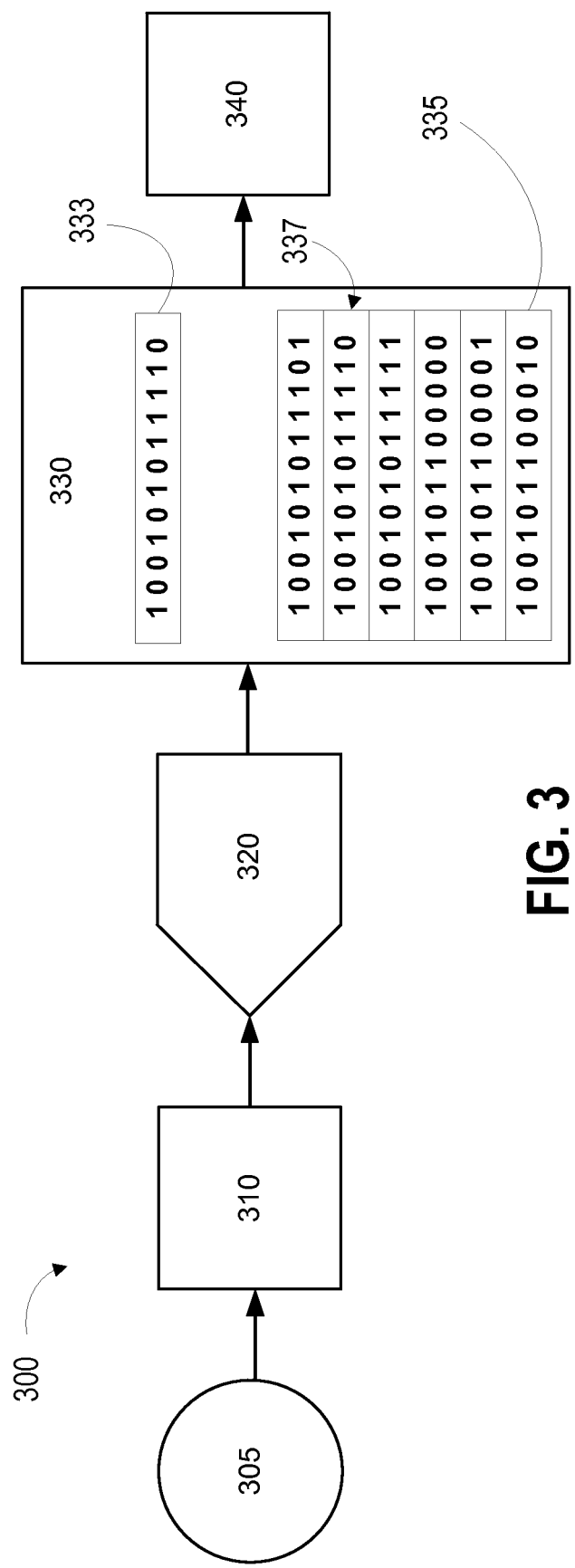
FIG. 3 is a block diagram of an example system that includes an analog-to-digital converter configured to generate digital codes related to an electrical signal generated by the system.

A sensing platform or other system as described herein could be configured to perform some other operations based on generated digital codes that are related to a physiological property of interest. A sensing platform could be configured to determine a health state or other information about a person based on the generated digital codes. As an illustrative example, FIG. 3 shows a system 300 configured to generate a plurality of digital codes related to a physiological property, to compare such generated digital codes to a set of specified digital codes, and to provide an indication responsive to such a determination (e.g., to a user, to a remote system). The system 300 includes a sensor 305 and a signal conditioner 310 configured to generate an electrical signal related to the physiological property. The system 300 further includes an analog-to-digital converter (ADC) 320 configured to generate digital codes based on the generated electrical signal.

The system further includes a controller 330 (e.g., a microcontroller, one or more integrated circuits) configured to receive the digital codes from the ADC 320 (indicated by a particular generated digital code 333 that is stored, e.g., in a register or other memory of the controller 330) and to compare the received digital codes (e.g., 333) to a set of specified digital codes. As illustrated in FIG. 3, the set of specified digital codes are individually stored in a memory 335 and include a matching code 337 that matches the particular generated digital code 333 (i.e., that has an identical binary value to the particular generated digital code 333). The controller 330 could also be configured to operate the sensor 305, signal conditioner 310, and/or ADC 320 to generate the digital codes. The system includes an alert indication circuit 340 configured to indicate (e.g., display, transmit) alerts responsive a determination that a received digital code (e.g., 333) matches one of the specified digital codes (e.g., 337). This could include providing an indication to a user via user interface elements, e.g., by providing a display (e.g., by providing an indication of a determined value of the physiological property, by providing an indication that the physiological property is outside of a specified range, by providing an indication that a user should apply a drug, seek medical assistance, or take some other action), providing a sound (e.g., a beep), by vibrating, or by providing some other indication to a user. Additionally or alternatively, the alert indication circuit 340 could provide an indication to an external system (e.g., a cellphone, an external reader device by, e.g., transmitted a wireless signal)

related to a received digital code (e.g., to indicate the digital code, to indicate that the digital code is outside of a specified range).

Comparing received digital codes that are related to a physiological property of interest to a specified set of digital codes (e.g., to determine a health state, to determine an alert state) could require less power and/or energy than determining values of the physiological property of interest, using the digital codes, and subsequently performing some comparison or other determination based on the determine physiological property value(s). As such, a system (e.g., 300) operating in this way could operate for extended periods of time (e.g., several weeks) while powered by a battery to provide alerts related to the physiological property of interest (e.g., to provide alerts related to a blood glucose level exceeding one or more specified thresholds).

A specified set of codes as described herein (e.g., the codes stored in the memory 335) could be specified in a variety of ways. In some examples (e.g., as shown in FIG. 3), the set of specified codes could be individually specified. Additionally or alternatively, the specified set of codes could be described by one or more thresholds, e.g., the specified set of codes could include the set of all codes having a binary value greater than a first threshold value and less than a second threshold value. Such a specified set of digital codes could include one or more sequences of sequential digital codes (i.e., digital codes having values that differ by one) or could include any other set of specified digital codes described by some other method.

Such a specified set of digital codes (e.g., the codes stored in the memory 335) could be provided by an external system (e.g., by an external reader in response to receiving a digital code form the device and receiving a measurement of the related physiological property from some other measurement system), could be determined by the device 300 (e.g., in response to a user inputting a known value of the related physiological property or some other information), or could be obtained by some other steps. In some examples, the system 300 could transmit a generated digital code to an external system (e.g., using a wireless transmitter of the alert indication circuit 340). The external system could then determine a set of digital codes corresponding to an alert condition, e.g., corresponding to an adverse health state (e.g., to a blood glucose level that is too high or too low). That is, the specified digital codes could correspond to such levels of the physiological property that correspond to the alert condition and that could be generated by the system 300 (e.g., by the ADC 320) when the physiological property has such levels.

Such a determination could include determining a relationship between digital codes generated by the system 300 and values of the physiological property based on a known value of the physiological property (e.g., a value detected by the external system, a value received by the external system by a user). For example, the external system could determine calibration data for the system 300 based on the generated digital code transmitted by the system 300 and the known value of the physiological property. The external system could then use the determined calibration data to determine a specified set of digital codes that the system 300 could generate when the physiological property has values corresponding to an alert condition (e.g., when a blood glucose level exceeds some threshold). The external system could then provide the determined specified set of digital codes (e.g., could provide one or more binary values of thresholds describing the specified set of digital codes) to the system 300 (e.g., by wirelessly transmitting information related to the specified set of digital codes).

III. EXAMPLE BIOSENSORS AND CALIBRATION DATA

Sensors configured to detect the presence, concentration, or some other property of physiological property of interest (e.g., a concentration or other properties of an analyte) could be configured in a variety of ways and incorporated into a variety of different systems or devices. For example, a sensor could be included on a distal end of a sensor probe that is configured to penetrate skin of a living body, such that the sensor can detect an analyte in interstitial (or other fluid) within the skin when the sensor probe penetrates the skin. Further, such sensor probes could be included as part of a body-mountable sensing platform that includes a flexible substrate, to which the sensor probe is attached, and that is configured to be mounted (e.g., by an adhesive layer or some other means) to a skin surface.

A sensor could detect the analyte electrochemically (e.g., by detecting a voltage between and/or a current passing through two or more electrodes), optically (by detecting an optical property of the analyte and/or some other element(s) of the environment and/or of the sensor), or by some other means. Such a sensor and/or electronics related thereto could generate an electrical signal related to the analyte (or other physiological property of interest), e.g., could generate a potentiometric voltage, an amperometric current, a voltage output of a photodetector that is related to an intensity of a received light, or some other electrical signal. Such a generated electrical signal could be used to perform some operations related to the physiological property of interest, e.g., could be used by an ADC to generate one or more digital codes that are related to the physiological property of interest and that can be used to determine a health state of a person, to determine a value of the physiological property, or according to some other application.

A sensor can be configured to detect an analyte by including one or more substances that selectively interact with the analyte. Such substances could have an electrical, optical, or other property that is related to the presence, concentration, or other property of the analyte. Additionally or alternatively, an analyte-selective substance could selectively react with and/or selectively catalyze a reaction of the analyte, and products of such a reaction could be detected by a sensor to allow for detection of the analyte. Analyte-selective substances can coat one or more surfaces of a sensor, can be incorporated into an analyte-permeable layer of polymer, gel, or some other material, or can be localized and/or incorporated on or into a sensor by some other method.

An electrochemical sensor includes at least two electrodes and is configured to electrochemically detect the analyte. This could include operating the two or more electrodes to detect a voltage between two or more of the electrodes, a current passing through one or more of the electrodes, an impedance of one or more of the electrodes, or some other electrochemical variable that can be related to one or more properties of the analyte. Electrodes of such an electrochemical sensor can be composed of one or more metals or metal alloys. Additionally or alternatively, electrodes can include conductive polymers or other conductive materials. The electrodes can be configured to have a specified ohmic resistance, to catalyze certain redox reactions with one or more chemicals (e.g., with the analyte, with a product of a reaction of the analyte that is catalyzed by an analyte-selective substance), to have a specified capacitance to a fluid, to have a stable electrode voltage relative to a fluid, or to have some other specified property.

An electrode configured to act as a reference electrode could be configured to provide a relatively stable voltage relative to a fluid with which it is in contact. Such configuration could include the composition of the reference electrode (e.g., the metal or other materials used to form the electrode), the structure of the reference electrode (e.g., the shape of the electrode, a micro-scale texture of the electrode, the configuration of multiple layers of material of the electrode), or other properties of a reference electrode. Further, such configuration could be related to properties of the fluid with which the electrode will be in contact and/or properties of the environment of the fluid and/or the electrode. For example, when the fluid is an aqueous fluid in regular contact with a sufficient source of oxygen (e.g., the fluid is a tear fluid or an eye), the reference electrode could include a surface layer composed of platinum (e.g., an approximately 100 nanometers to approximately 1 micron thick layer of platinum). In another example (e.g., where the fluid is an aqueous fluid that does not have access to a sufficient source of oxygen), the reference electrode could include a layer of silver chloride formed on a layer of silver (e.g., with a combined thickness of the silver and silver chloride layers being between approximately 2 microns and approximately 20 microns). Such a silver/silver chloride electrode could be formed by depositing a layer of silver and subsequently forming a silver chloride layer atop the silver layer by anodically oxidizing the silver layer. Such anodic oxidization could include submerging the deposited silver layer in an acidic solution containing a source of chloride ions (e.g., a 1M solution of hydrochloric acid) and passing a current through the silver layer to cause the chloride in the solution to form silver chloride on the silver layer.

An electrode configured to act as a working electrode could be made selectively sensitive to an analyte by immobilizing a substance (e.g., a reagent, a protein, an enzyme) that selectively interacts with the analyte on or near the working electrode of the sensor. Such an analyte-selective substance can be immobilized on the surface of the working electrode by crosslinking the substance into a crosslinked layer on the surface of the electrode. This could include using an aldehyde, dialdehyde (e.g., glutaraldehyde), or other crosslinking agents to form the crosslinked layer of the substance on the electrode surface. Additionally or alternatively, such an analyte-selective substance can be localized within an analyte-permeable polymer layer that is disposed on the working electrode.

The analyte-selective substance can be disposed within a polymer layer formed on the surface of the working electrode. Such a polymer layer can be permeable to the analyte and contain a reagent that selectively reacts with the analyte to create a reaction product that can be sensed directly by an electrode and/or by some other element (e.g., a fluorophore or other substance that selectively interacts with the reaction product). In some examples, the polymer layer is a hydrogel that includes 2-hydroxyethyl methacrylate units. Such a hydrogel could contain additional polymer units or other chemicals to adjust a permeability of the hydrogel to the analyte, to bind the analyte-selective substance within the hydrogel, to increase a degree of crosslinking of the hydrogel, or to specify one or more other properties of the hydrogel. For example, such a hydrogel could additionally include di(ethylene glycol) dimethacrylate units. The polymer layer could be formed on the working electrode by forming a solution containing monomer units (e.g., units of 2-hydroxyethyl methacrylate), crosslinker units (e.g., units of di(ethylene glycol) dimethacrylate), copolymer units, the analyte-selective substance, and/or a polymerization initiator (e.g., the photoinitiator 2,2-dimethoxy-2-phenylacetophenone), depositing the formed solution on the working electrode, and polymerizing the solution into the polymer layer containing the analyte-selective substance. In some examples, a permeability, thickness, or other properties of such an analyte-permeable layer could be specified to control a rate of diffusion of the analyte from interstitial fluid to the surface of the working electrode (e.g., the polymer layer could have a thickness between approximately 5 microns and approximately 20 microns).

In some examples, the analyte-selective substance could be configured to selectively cause a chemical reaction of the analyte, and one or more reaction products of the reaction could be detected (e.g., potentiometrically, amperometrically) by the working electrode. For example, the analyte-selective substance could include an agent that selectively oxidizes and/or reduces the analyte (e.g., the analyte-selective substance could be an oxidoreductase enzyme or protein). For example, the analyte could be glucose, pyruvate, or urea and the analyte-selectively substance could be glucose oxidase, pyruvate oxidase, or urease, respectively. Such a reaction could produce reaction products including oxides (e.g., hydrogen peroxide) and the working electrode could be configured to detect those oxides. For example, the reaction products could include hydrogen peroxide and the working electrode could include a layer platinum (e.g., a layer of platinum having a thickness between approximately 1 micron and approximately 5 microns).

The areas of electrodes of a sensor could be specified according to an application. For example, the area of a working electrode of an amperometric sensor could be specified such that the sensor has a specified current gain (i.e., such that a relationship between a measured current through the working electrode and the concentration of an analyte in fluid to which the working electrode is exposed has some specified value and/or has some value within some specified range of values). For example, a working electrode of an amperometric sensor could have an area between approximately 0.05 square millimeters and approximately 0.5 square millimeters. Further, a reference electrode of an amperometric sensor could have an area sufficiently large that, when a return current passes through the reference electrode, the relative voltage between the reference electrode and the fluid to which the reference electrode is exposed is within an acceptable range of the zero-current relative voltage of the reference electrode. For example, a reference electrode of an amperometric sensor could have an area between approximately 0.5 square millimeters and approximately 3.0 square millimeters.

In some examples, the sensor of a sensing platform can include an analyte-selective substance that has an optical property that is related to the presence, concentration, or some other property of the analyte. For example, the substance could include a fluorophore having a fluorescence intensity, a fluorescence lifetime, an emission wavelength, an excitation wavelength, or some other fluorescence property that is related to the analyte. Additionally or alternatively, a color, saturation, absorption spectrum, or some other optical property of a substance disposed at the end of a sensor probe could be related to the presence, concentration, or some other property of the analyte. The sensor and/or a sensor platform including the sensor could include a light emitter and/or a light detector configured to illuminate and/or to receive light emitted from the analyte-sensitive substance, respectively, in order to determine the optical property of the substance that is related to the analyte. Such a light detector could be configured to generate an electrical signal related to the analyte (or other physiological property of interest), e.g., to generate an electrical signal related to the optical property of the analyte-sensitive substance.

In some examples, such an analyte-selective substance could be disposed in a layer of polymer, gel, or other analyte-permeable material disposed at the distal end of an optical fiber. Additionally or alternatively, a protective layer could be disposed over the analyte-permeable material. In some examples, the optical fiber could be disposed on (e.g., adhered to, formed on) a flexible substrate that is, in turn, continuous with a flexible substrate that is configured to be mounted to a skin surface and on which electronics (including, e.g., a light emitter and/or light detector) could be disposed. Further, one or both of a light emitter and light detector could be disposed proximate the analyte-selective substance such that the light emitter and/or light detector could illuminate and/or receive emitted light from, respectively, the analyte-selective substance directly rather than through an optical fiber. In such examples, the light emitter, light detector, and/or analyte-selective substance could be disposed on the distal end of a sensor probe as described in connection with other embodiments described herein.

A protective layer disposed over a sensor as described herein (e.g., an electrochemical sensor, an optical sensor) could be formed by a variety of processes, including CVD, application of a monomer solution followed by polymerization, precipitation of elements of the protective layer from a solution into which the sensor has been dipped, or some other methods. For example, the sensor (and/or some terminal aspect thereof, e.g., a specified length of the distal end of an elongate sensor probe at the distal end of which a sensor is disposed) could be dipped in a solution containing a monomer, co-monomer, crosslinker, and/or other chemicals (e.g., units of 2-hydroxethyl methacrylate and/or units of di(ethylene glycol) dimethacrylate), and the solution applied to the sensor could then be polymerized to form the protective layer.

Electrical signals and/or digital codes related to a physiological property of interest that are generated by a device (e.g., 100, 200, 300) could be related to the physiological property of interest in a variety of ways. Such relationships could be related to properties of a sensor, an ADC, an amplifier, or other elements of the device (e.g., related to a gain, offset, or other operational parameters of such devices). Such relationships could additionally be related to properties of the interface between a sensor and tissues or other environments of interest. For example, the physiological property of interest could be a blood glucose level, and a relationship between digital codes generated by a device and the blood glucose level could be related to a level of perfusion of tissues surrounding a sensor of the device, a property of glucose transport form blood vessels into the interstitial space near the sensor, or related to other properties of such tissues and/or properties of the device. Such relationships could change over time, e.g., related to changes in the tissue. For example, such a relationship could change related to changes in a level of perfusion of tissue near a sensor.

Calibration data related to such relationships could be used to determine values of a physiological parameter based on digital codes generated (e.g., by an ADC) by a system configured to detect such properties. Such calibration data could include information describing such relationships, e.g., could describe a calibration curve relating binary values of the digital codes to values (e.g., concentrations) of the physiological property. For example, such calibration data could include offset values that could be digitally added or subtracted from the digital codes, gain values that could be used to scale digital codes, coefficient values of terms of a polynomial, or other information. In some examples, calibration data could include lookup tables or other information describing, for one or more particular digital codes, corresponding values of the physiological property.

Figure 4A:
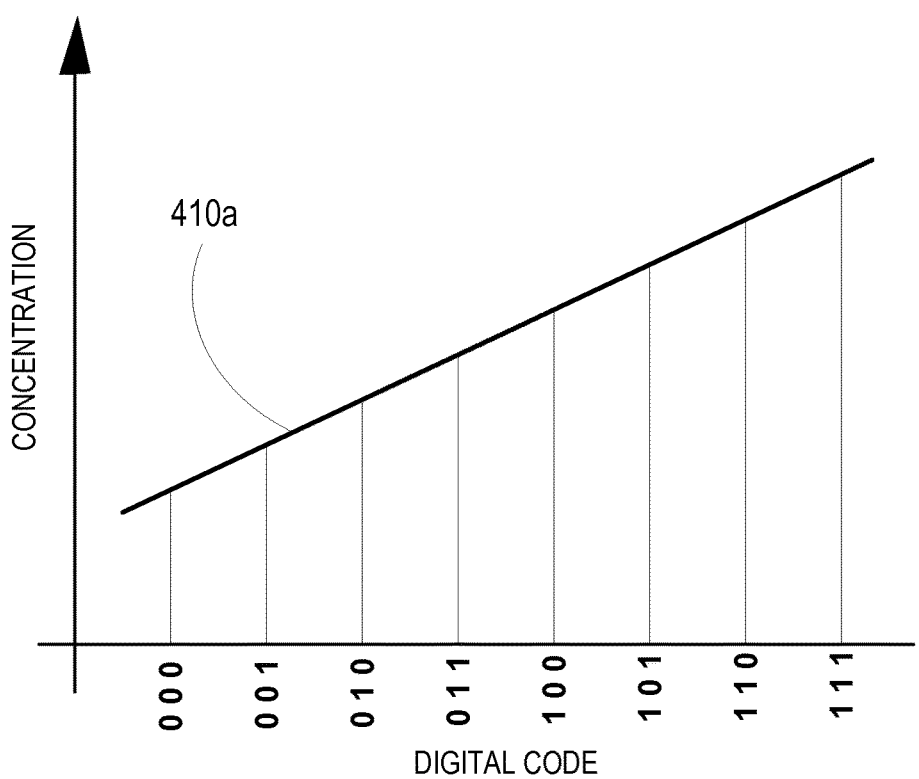
FIG. 4A is a calibration curve relating digital codes to related values of a physiological property.
Figure 4B:
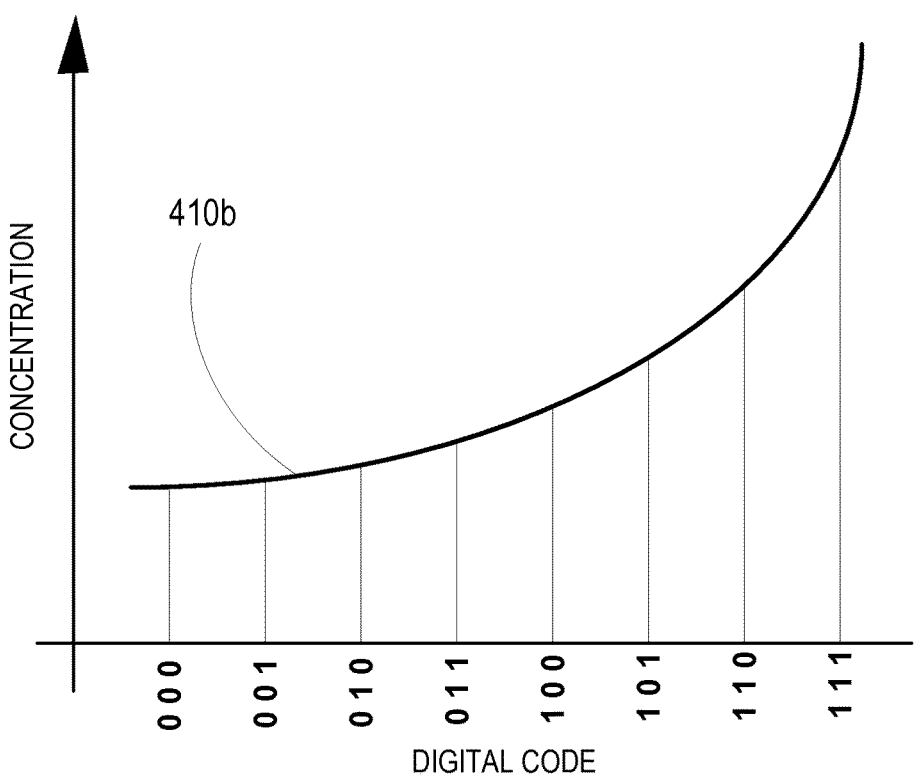
FIG. 4B is a calibration curve relating digital codes to related values of a physiological property.

As an illustrative example, FIG. 4A shows an example of a linear calibration curve 410*a* relating digital codes to values of a concentration of an analyte of interest. Such a linear relationship could be described by calibration data that includes an offset value and a gain value. For example, a controller of a device could add an offset value to a generated digital code and then apply a gain value (e.g., by operating a hardware logic multiplier or other logic elements) to the offset digital code to generate a digital representation of a determined value of the concentration of the analyte of interest. In another example, FIG. 4B shows an example of a nonlinear calibration curve 410*b* relating digital codes to values of a concentration of an analyte of interest. Such a nonlinear relationship could be described by calibration data that includes an offset value, one or more polynomial coefficient values, one or more exponential coefficients, or some other values describing the nonlinear calibration curve 410*b* and/or that could be used to determine a concentration value based on a digital code.

Calibration data could describe a polynomial relationship, an exponential relationship, a sinusoidal relationship, or some other relationship between digital codes (and/or binary values thereof) and concentrations or other physiological properties of interest. In some examples, such relationships could be piecewise-defined relationships, i.e., different ranges or sets of digital codes could be related to physiological property values by respective different calibration data. For example, a first set of digital codes could be related to analyte concentration values by a linear relationship (e.g., by calibration data that includes an offset and a gain) while a second set of digital codes could be related to analyte concentration values by a nonlinear relationship (e.g., by calibration data that includes two or more polynomial coefficient values). Further, in some examples the calibration data could include a lookup table or similar information used to define one or more physiological property values corresponding to respective one or more digital codes.

Moreover, it is particularly noted that while analyte sensors (or other sensors of other physiological properties of interest) and body-mountable sensor platforms including such sensors are described herein by way of example as a body-mountable, skin-penetrating and/or skin-surface-mounted devices, it is noted that the disclosed sensors, electrode arrangements, and sensing platforms can be applied in other contexts as well. For example, sensors and sensing platforms disclosed herein may be included in body-mountable and/or implantable sensors and/or sensing platforms used to measure an analyte in a fluid of an animal (or to detect some other physiological property of interest of the animal). In another example, sensors and/or sensing platforms disclosed herein may be included in devices to measure an analyte in or other property of an environmental fluid, such as a fluid in a river, lake, marsh, reservoir, water supply, sanitary sewer system, or storm sewer system. In another example, sensors and/or sensing platforms disclosed herein may be included in devices to measure an analyte in or other property of a fluid which is part of a process, such as a waste treatment process, pharmaceutical synthesis process, food preparation process, fermentation process, or medical treatment process

IV. EXAMPLE FLEXIBLE BIOSENSOR PLATFORM

Figure 5A:
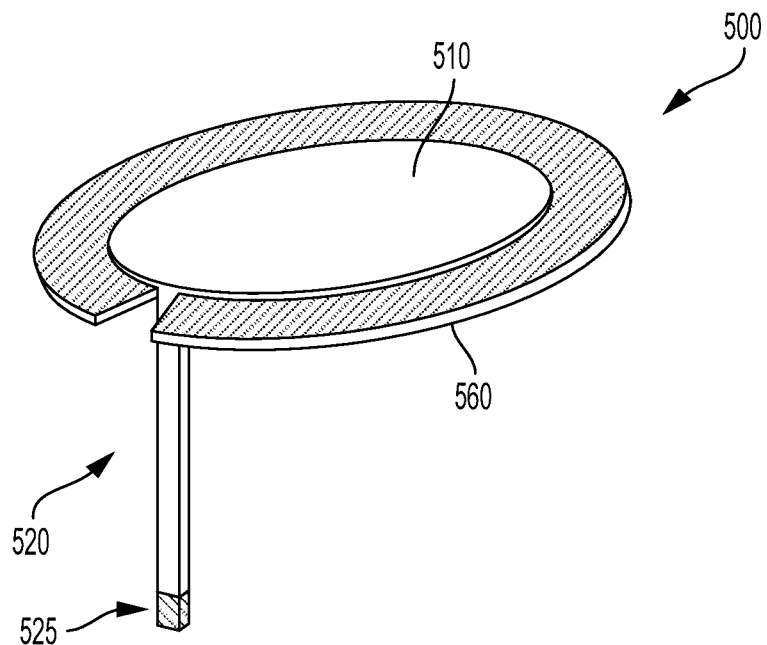
FIG. 5A is a top aspect view of an example body-mountable device.
Figure 5B:
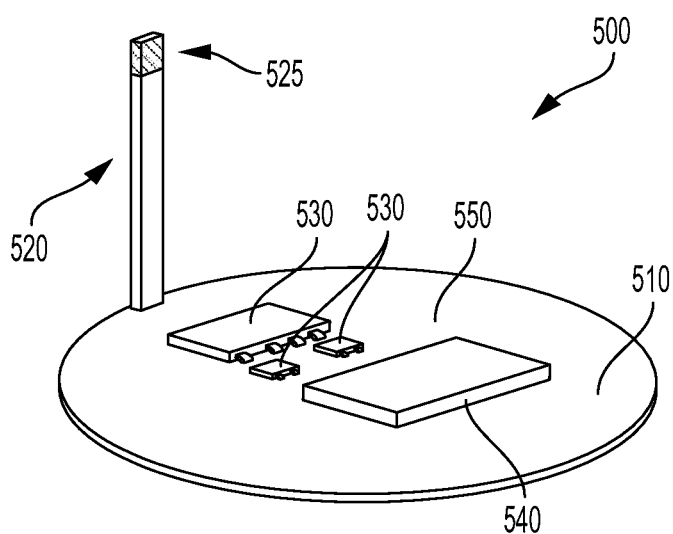
FIG. 5B is a bottom aspect view of the example body-mountable device shown in FIG. 5A.

FIG. 5A is a top view of an example body-mountable sensing platform 500. FIG. 5B is a bottom view of the example body-mountable sensing platform shown in FIG. 5A. It is noted that relative dimensions in FIGS. 5A and 5B are not necessarily to scale, but have been rendered for purposes of explanation only in describing the arrangement of the example body-mountable sensing platform 500. The body-mountable device 500 is formed of a flexible substrate 510 shaped (as an illustrative example) as a circular disk. A sensor probe 520 extends from the flexible substrate 510 and is configured to penetrate a skin surface (e.g., to penetrate into skin of the upper arm or abdomen of a human body). A sensor 525 is disposed at a distal end of the sensor probe 520. The sensor 525 is configured to detect an analyte (e.g., glucose) in interstitial or other fluids under and/or within the skin when the sensor probe 520 penetrates the skin. An adhesive layer 560 is provided to mount the flexible substrate 510 to a skin surface (the adhesive layer 560 is not shown in FIG. 5B, to allow illustration of elements of the body-mountable sensing platform 500 that are disposed on the bottom surface 550 of the flexible substrate 510).

The body-mountable sensing platform 500 additionally includes electronics 530 disposed on the flexible substrate 510 and configured to provide various applications of the sensing platform 500 including, e.g., operating the sensor 525 to generate a plurality of digital codes (e.g., using an ADC of the electronics 530) related to the analyte, recording such generated digital codes in a memory of the electronics 530, determining values of a property of the analyte (e.g., concentration values) based on such generated digital codes, and/or indication such generated digital codes and/or values of related physiological properties determined therefrom (e.g., by using an antenna to wirelessly indicate such information) to an external system and/or to a user (e.g., via a display or other user interface elements). The antenna (not shown) could be configured as a loop antenna on bottom surface 550 (e.g., encircling electronics 530), or the antenna could be configured as a chip antenna or some other configuration. A battery 540 is provided to power the body-mountable sensing platform 500 (e.g., to power the electronics 530). Components (e.g., antennas, batteries, electronics, user interface elements) could additionally or alternatively be disposed on the top surface of the flexible substrate 510 (i.e., the surface of the flexible substrate 510 opposite the bottom surface 550).

The flexible substrate 510 is configured to be mounted to a skin surface. In the example shown in FIGS. 5A and 5B, this includes a layer of adhesive 560 being provided to adhere the flexible substrate 510 to a skin surface. Additional or alternative means could be provided to mount the flexible substrate 510 to a skin surface. For example, a liquid or gel adhesive could be applied to the skin surface and/or to the flexible substrate 510 to mount the flexible substrate 510 to the skin surface. The flexible substrate 510 could be placed on the skin surface and secured using tape or other adhesives. In some examples, the body-mountable sensing platform 500 could include a dry adhesive configured to removably mount the flexible substrate 510 to a skin surface. Other means for mounting the flexible substrate 510 or other elements of the body-mountable sensing platform 500 to a skin surface or to other elements or aspects of a living body are anticipated. Further, in some embodiments, a body-mountable sensing platform 500 could be provided that is configured to be emplaced proximate a target fluid (e.g., interstitial fluid, synovial fluid, blood, tears, saliva, mucus) without mounting to a skin surface or other tissue surface. For example, a body-mountable sensing platform 500 as described herein could be configured to be placed between the teeth and cheek of a living body, on the eye of a living body, or at some other location of a living body without being mounted to a particular tissue surface.

The flexible substrate 510 can have a thickness, shape, composition, and/or other properties specified such that the flexible substrate 510 can be mounted to a skin surface of a living body and further such that such mounting minimally interferes with activities of the living body (e.g., motions of the living body). This could include the flexible substrate 510 being sufficiently flexible that mounting of the flexible substrate 510 to the skin surface causes a minimum of discomfort. The flexible substrate 510 could be composed of polyimide or some other flexible polymeric or other material. The flexible substrate could have a thickness less than approximately 100 microns. Further, the flexible substrate 510 could have a size specified to minimally interfere with activities of the living body. For example, the flexible substrate 510 could have size (e.g., a diameter of a circular portion, as illustrated in FIGS. 5A and 5B) less than approximately 11 millimeters. Diameter and thickness values are provided for explanatory purposes only. Further, the shape of the flexible substrate 510 could be different from that illustrated in FIGS. 5A and 5B or elsewhere herein; for example, the flexible substrate 510 could have an elongate shape, a square or rectangular shape, or some other shape according to an application.

For example, the flexible substrate 510 could have an elongate shape to provide sufficient area for disposition of electronics, batteries, antennas, or other components on the flexible substrate 510 while minimally impeding motion and/or deformation of the skin surface to which the flexible substrate 510 is mounted (e.g., by being formed and/or mounted to the skin surface such the orientation of the elongate shape of the flexible substrate 510 is perpendicular to a direction of strain of the skin surface).

One or more surfaces of the flexible substrate 510 (e.g., the bottom surface 550) could be used as a platform for mounting electronics such as chips (e.g., via flip-chip mounting) and for patterning conductive materials (e.g., via deposition techniques) to form electrodes, antenna(e), and/or connections. The composition of the flexible substrate 510 could be chosen to allow for the formation and/or disposition of such elements of the body-mountable sensing platform 500. For example, the flexible substrate 510 could be composed of polyimide or some other polymeric and/or metallic material(s) such that metal contacts, traces, and interconnects can be patterned directly on the surface of the flexible substrate 510 (e.g., by sputtering, CVD, or some other deposition process) and/or on a coating or layer formed on one or more surfaces of the flexible substrate 510. Further, such patterned structures and/or other elements disposed on the flexible substrate 510 (e.g., electronics 530, battery 540, antennas) could, in combination with the flexible substrate 510, have a thickness or other property specified to provide the overall body-mountable sensing platform 500 with flexibility. For example, the flexible substrate 510 in combination with electronics 530 and battery 540 disposed thereon could have a thickness less than approximately 0.5 millimeters.

The electronics 530 disposed on the flexible substrate 510 could include a variety of devices. For example, the electronics 130 could include an antenna (e.g., a chip antenna), a microcontroller, amplifiers, analog-to digital converters, light emitters, light detectors, temperature sensors, transmitters, radios, transceivers, or some other component or components. Such components can be mounted to and/or electrically connected via interconnects or traces patterned on the flexible substrate 510. Further, antennas, electrodes, capacitors, resistors, or other components could be formed from such traces or other interconnects formed on the surface of the flexible substrate 510. The electronics 530 can include logic elements configured to operate the sensor 525 to generate digital codes related to an analyte or other physiological property, an antenna (e.g., a loop, dipole, or other type of antenna formed on the flexible substrate 510, a chip antenna disposed on the flexible substrate 510) to wirelessly indicate information (e.g., digital codes, physiological property values determined therefrom), and/or to provide other functions. A loop, dipole, or other type of antenna can be one or more layers of conductive material patterned on a surface (e.g., 550) of the flexible substrate 510 to form one or more specified conductive shapes (e.g., a ring, a spiral, a curved or straight line, an elliptical or rectangular patch, a fractal). Electrical interconnects (e.g., traces), antennas, and/or conductive electrodes (e.g., for an electrochemical analyte sensor, etc.) can be formed from conductive materials patterned on the flexible substrate 510 by a process for precisely patterning such materials, such as deposition, lithography, etc. The conductive materials patterned on the flexible substrate 510 can be, for example, gold, platinum, palladium, titanium, carbon, aluminum, copper, silver, silver-chloride, conductors formed from noble materials, metals, combinations of these, etc.

The sensor probe 520 is an elongate element of the body-mountable sensing platform 500 that is configured to penetrate a skin surface such that the sensor 525 located at the distal end of the sensor probe 520 is in contact with a fluid (e.g., interstitial fluid, blood) containing an analyte of interest (e.g., glucose) when the sensor probe 520 is penetrating the skin. For example, the sensor probe 520 could be more than approximately 2 millimeters long. The sensor probe 520 could have a length or other properties specified such that, when the sensor probe 520 penetrates skin and/or the flexible substrate 520 is mounted to a skin surface, a sensor (e.g., 525) or other element(s) disposed on the sensor probe 520 contact tissue at a specified depth within the skin (e.g., tissue of the dermis of the skin, subcutaneous tissue). For example, the sensor probe 520 could have a length between approximately 500 microns and approximately 6000 microns. Further, the sensor probe 520 could have one or more dimensions specified to provide sufficient area for electrodes or other elements disposed on the sensor probe 520, to minimally interfere with the skin (e.g., by requiring a minimal incision or other alteration of the skin to provide for penetration of the sensor probe 520), or according to some other application. For example, the sensor probe 520 could have a width between approximately 25 microns and approximately 400 microns.

The sensor probe 520 could be composed of a variety of materials and elements formed by a variety of processes. The sensor probe 520 could be composed of a flexible material (e.g., polyimide) or a relatively inflexible material; further, a thickness, width, shape, or other properties of the sensor probe 520 could be specified to provide a degree of flexibility or inflexibility. For example, a flexible sensor probe 520 could have a width between approximately 25 microns and approximately 400 microns and/or a thickness less than approximately 100 microns. In some examples, the sensor probe 520 could be formed from the same material as the flexible substrate 510; i.e., the sensor probe 520 could be an elongate portion of the flexible substrate 510 that extends from a portion of the flexible substrate 510 that is configured to be mounted to a skin surface and/or on which electronics 530 or other components are disposed. Alternatively, the sensor probe 520 could be attached to the flexible substrate 510. For example, the sensor probe 520 could include optical fiber(s), flexible element(s) (e.g., an elongate piece of polyimide or other polymeric or metallic substance), wire(s), elongate pieces of shaped silicon, or other elements adhered, welded, bonded, or otherwise attached to the flexible substrate 510. Alternatively, such sensor probes could be used for other applications and/or in combination with components or devices other than a flexible substrate (e.g., 510) as described herein.

The sensor probe 520 could be configured to pierce skin to allow the sensor probe 520 to penetrate the skin and dispose the sensor 525 in contact with interstitial or other fluids within the skin. For example, the sensor probe 520 could be sharpened, could include one or more rigid materials to facilitate application of force to the sensor probe 520 to pierce the skin (e.g., stainless steel tubes, rods, sheets, and/or needles), or could be otherwise configured to pierce skin. In some examples, the sensor probe 520 could include materials having a stiffness or some other property that changes to allow the sensor probe 520 to be used to pierce the skin during a first period of time and subsequently to become less rigid or to change some other property according to an application. In some examples, the sensor probe 520 could include a material configured to initially have a high rigidity, to allow for piercing of skin, and to soften when the sensor probe penetrates the skin for a period of time. For example, the sensor probe 520 could include a piece of poly-2-hydroxyethyl methacrylate (poly-HEMA) or some other hydrogel configured to soften by absorbing water (e.g., from interstitial fluid) once the sensor probe 520 has penetrated the skin. In another example, the sensor probe 520 could include a stiff material that is configured to dissolve into and/or be absorbed by the skin (e.g., polylactic acid (PLA)).

Additionally or alternatively, the sensor probe 520 could be inserted into skin by another device that is configured to pierce the skin, or into an incision into the skin formed by another device. For example, the sensor probe 520 could be configured to be mounted within the channel of a half-needle of a device (e.g., a device configured to insert the sensor probe 520 into skin and/or to mount the flexible substrate 510 to a skin surface) such that the half-needle could pierce the skin and subsequently be retracted, leaving the sensor probe 520 in place penetrating the skin.

Note that the depiction of a body-mountable sensor platform 500 having a single sensor probe 520 on a distal end of which a single sensor 525 is disposed is intended as a non-limiting, illustrative example. A particular sensor probe of a body-mountable sensing platform could include additional sensors disposed at different locations on the particular sensor probe. For example, a particular sensor probe could include a plurality of sensors disposed along the length of the particular sensor probe to allow for detection of some property of skin (e.g., a concentration of an analyte within the skin) at a variety of depths within the skin. A body-mountable sensor platform could include more than one sensor probe and such more than one sensor probes could have respective widths, lengths, thicknesses, sensors, sensor locations, or other properties. Further, a body-mountable sensing platform could include sensors that are not disposed at a distal end or other locations on a sensor probe. For example, one or more sensors could be disposed on a flexible substrate (e.g., 510) or other element(s) of such a body-mountable sensing platform.

A sensor disposed at a distal end of a sensor probe or at some other location of a body-mountable sensing platform as described herein could include a variety of components and/or substances configured in a variety of ways. In some examples, such sensors could include one or more substances that selectively interact with an analyte. For example, such substances could include proteins, enzymes, aptamers, DNA, RNA, nano-structures, antibodies, reagents, nano-structured surfaces, or other substances configured to selectively bind to, catalyze a reaction of, or otherwise selectively interact with an analyte of interest. Such an analyte-sensitive substance could be disposed on a surface of a sensing platform (e.g., on a metal surface of an electrode, on a surface of an optical fiber, on some other surface of a sensor probe and/or flexible substrate) and/or within a polymer, gel, or other layer that is permeable to the analyte and that is disposed on such a surface.

In some examples, an analyte-selective substance could be disposed on a surface of a sensing platform (e.g., on an electrode surface) by crosslinking the substance on the surface (e.g., using glutaraldehyde to crosslink the analyte-sensitive substance). In some examples, an analyte-selective substance can be disposed within a polymer layer formed on a surface of a sensing platform. Such a polymer layer can be permeable to the analyte and contain a reagent that selectively reacts with the analyte to create a reaction product that can be sensed directly by an electrode and/or by some other element (e.g., a fluorophore or other substance that selectively interacts with the reaction product). In some examples, the polymer layer that contains the analyte-selective substance is a hydrogel that includes 2-hydroxyethyl methacrylate units. Such a hydrogel could contain additional polymer units or other chemicals to adjust a permeability of the hydrogel to the analyte, to bind the analyte-selective substance within the hydrogel, in increase a degree of crosslinking of the hydrogel, or to specify one or more other properties of the hydrogel. For example, such a hydrogel could additionally include di(ethylene glycol) dimethacrylate units.

In some examples, the sensor of a sensing platform can include two or more electrodes configured to detect or measure the analyte electrochemically. The two or more electrodes could include a working electrode selectively sensitive to the analyte and a reference electrode. In some examples, exposing the sensor to a target fluid (e.g., interstitial fluid) causes a potentiometric voltage to develop between the working electrode and the reference electrode that can indicate the concentration of the analyte near the working electrode. Additionally or alternatively, a specified voltage could be applied between the reference electrode and the working electrode and an amount of current that responsively flows through the working electrode could be related to the concentration of the analyte near the working electrode and/or the rate at which the analyte diffuses to the working electrode (e.g., through a hydrogel layer containing an analyte-selective substance and/or through a hydrogel layer disposed to protect the working electrode and/or other components of the sensor).

In some examples, the sensor of a sensing platform can include an analyte-selective substance that has an optical property that is related to the presence, concentration, or some other property of the analyte. For example, the substance could include a fluorophore having a fluorescence intensity, a fluorescence lifetime, an emission wavelength, an excitation wavelength, or some other property that is related to the analyte. Additionally or alternatively, a color, saturation, absorption spectrum, or some other optical property of a substance disposed at the end of the sensor probe could be related to the presence, concentration, or some other property of the analyte. The sensor platform could include a light emitter and/or a light detector configured to illuminate and to receive light emitted from the analyte-sensitive substance, respectively, in order to determine the optical property of the substance that is related to the analyte. In some examples, a sensor probe of the sensing platform could include an optical fiber and the analyte-selective substance could be disposed on a distal end of such an optical fiber. In such examples, a light emitter and/or a light detector could be disposed at a proximal end of the optical fiber, such that the light emitter and light detector illuminate and received light from the analyte-sensitive substance via the optical fiber. In such examples, the light emitter and/or light detector could be disposed on a flexible substrate of the sensor platform (e.g., as part of electronics disposed on the flexible substrate).

In some examples, a polymer, gel, or other layer that is permeable to the analyte could be disposed over to one or more components of the sensor (e.g., over a working electrode, over a layer containing and/or composed of an analyte-selective substance) and/or other elements of a sensing platform to protect the elements of the sensing platform or according to some other application. In some examples, a permeability, thickness, or other properties of such an analyte-permeable layer (and/or of a similar layer containing an analyte-selective substance) could be specified to control a rate of diffusion of the analyte from interstitial fluid to a sensor (e.g., to a metal electrode surface of the sensor) or to some other element of the sensing platform (e.g., to an analyte-selective substance disposed proximate to an electrode, optical fiber, or some other element of the sensing platform). In some examples, a protective or other polymer layer could be a hydrogel, e.g., a hydrogel that includes units of 2-hydroxethyl methacrylate and/or units of di(ethylene glycol) dimethacrylate.

The body-mountable devices as shown herein (e.g., 100, 200, 300, 500) could include one or more sensors (not shown) configured to detect physiological properties of a body (e.g., concentrations of analytes in blood, sweat, tears, or other bodily fluids, an amount of blood in a portion of subsurface vasculature, an oxygenation state of blood), properties of the environment of the device (e.g., an ambient illumination, a barometric pressure, a temperature), properties of the device (e.g., an acceleration, an orientation), or to detect some other information. Such sensors could include accelerometers, electrodes (e.g., electrodes of an electrochemical analyte sensors, electrodes of an electrophysiological sensor configured to detect a galvanic skin potential, an electrocardiogram, an electrooculogram, an electromyogram, or some other bioelectrical signal), light detectors, thermometers, gyroscopes, capacitance sensors, pressure sensors, strain gauges, light emitters, microphones, or other elements configured to detect one or more physical variables related to a property of interest.

The body-mountable devices as shown here could operate such elements to measure physiological parameters or other information of interest at one or more points in time using power provided by an electrochemical battery and/or power provided by some other source (e.g., RF power provided by an external system via an antenna of a body-mountable device). This could include generating electrical signals related to such properties of interest (e.g., signals having voltages, current, frequencies or other properties related to the properties of interest) and further generated digital codes based on such generated electrical signals (e.g., using one or more ADCs). Such generated digital codes could be recorded (e.g., in a memory of the device, for example, for later transmission to an external system), transmitted to an external system, indicated using elements of the device (e.g., using a display, using one or more light-emitting elements), used to determine a value of the property of interest, used to determine a health state of a user, or used according to some other application.

Although devices are described herein by way of example as body-mountable devices, it is to be understood that the disclosed embodiments can be applied in other contexts as well. For example, embodiments as disclosed herein may be included in implantable devices. In some contexts, devices as described herein are situated to be substantially encapsulated by a biocompatible polymeric material suitable for being in contact with an external body surface and/or for being implanted. In one example, a mouth-mountable device is configured to be mounted within an oral environment, such as adjacent a tooth or adhered to an inner mouth surface. In another example, an implantable medical device may be encapsulated in biocompatible material and implanted within a host organism.

V. EXAMPLE METHODS

Figure 6:
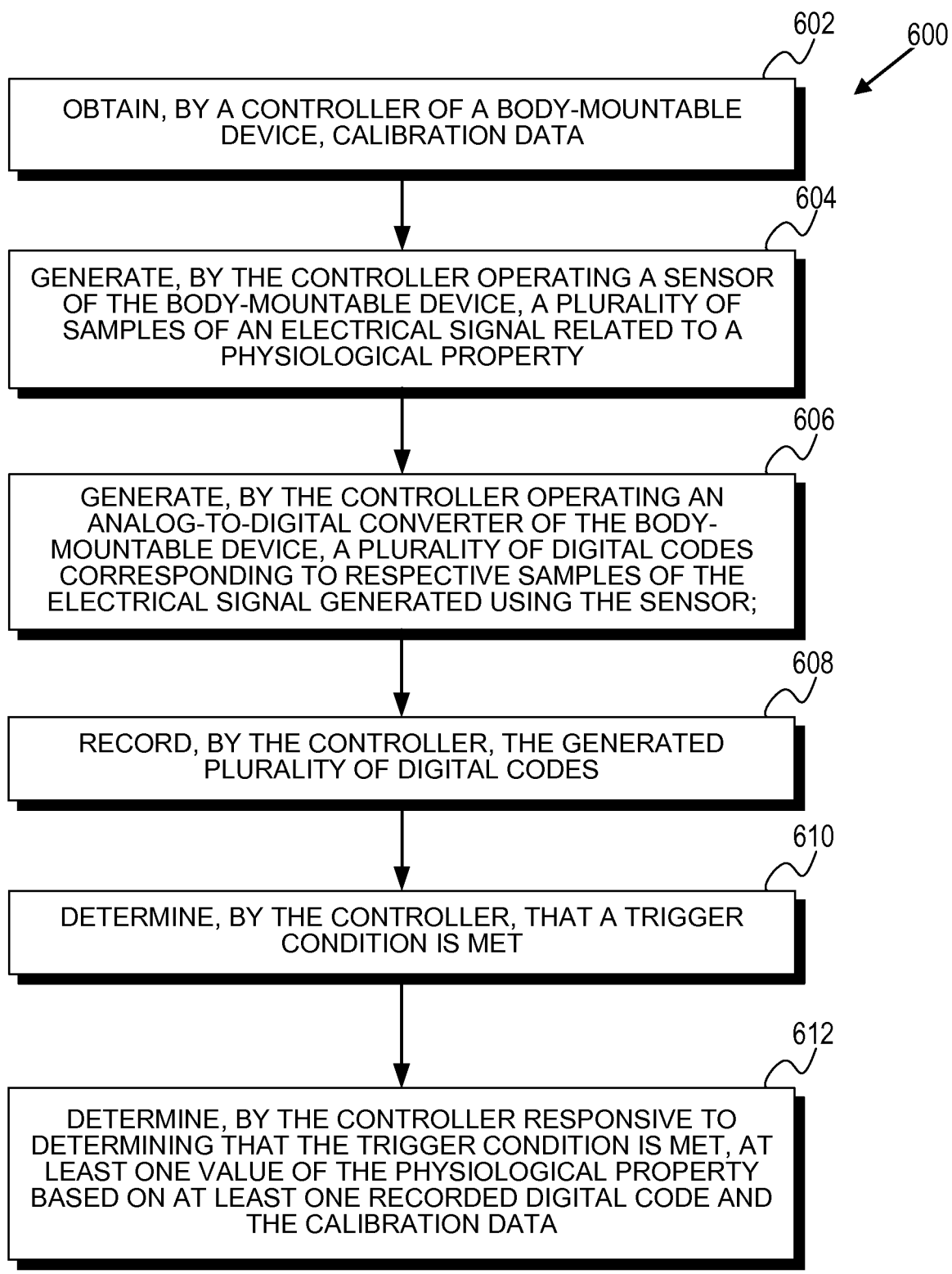
FIG. 6 is a flowchart of an example process for operating a body-mountable device.

FIG. 6 is a flowchart of a method 600 for operating a body-mountable device to detect a physiological property (e.g., a concentration of an analyte in a fluid) of a body. The body-mountable device includes (i) a flexible substrate configured to be mounted to a skin surface, (ii) a sensor that is configured to generate an electrical signal that is related to the physiological property, (iv) an analog-to-digital converter (ADC) that is configured to receive the generated electrical signal and to generate digital codes related to the received electrical signal, wherein the analog-to-digital converter is disposed on the flexible substrate, and (v) a controller that is disposed on the substrate and that is operably coupled to the ADC. Operating the body-mountable device to detect a physiological property includes the controller performing the illustrated steps of the method.

The method 600 includes obtaining, by the controller, calibration data (602). This could include receiving information relating to the calibration data (e.g., an offset, gain, or other calibration data values, a value of the physiological property detected using some other system) from a user (e.g., via buttons or other elements of a user interface) and/or from some external system (e.g., via a wireless communications interface). Additionally or alternatively, obtaining calibration data (602) could include the body-mountable device determining the calibration data, e.g., based on information detected using the sensor, based on inputs from a user interface (e.g., an input known value of the physiological parameter), based on an output of some further sensor of the body-mountable device, or according to some other method.

The method 600 includes generating, by the controller operating the sensor, a plurality of samples of the electrical signal related to the physiological property (604). This could include applying a voltage and/or current to electrodes of an electrochemical sensor (e.g., to a reference and/or working electrode of an electrochemical analyte sensor). Generating a plurality of samples of the electrical signal (604) could include operating a light detector and/or light emitter to generate samples of an electrical signal relating to an optical property of an analyte-sensitive substance having such an optical property that is related to the physiological property. Generating a plurality of samples of the electrical signal (604) could include generating the electrical signal continuously across the plurality of samples (e.g., maintaining a current through electrodes of an electrochemical sensor during an extended period of time that includes the timing/time periods of the plurality of samples). Alternatively, generating a plurality of samples of the electrical signal (604) could include intermittently operating the sensor and/or other elements of the body-mountable device (e.g., operating a light emitter and a transimpedance amplifier that is connected to alight detector to generate a signal related to an optical property of an analyte-sensitive substance during a plurality of time periods corresponding to the plurality of samples).

The method 600 includes generating, by the controller operating the ADC, a plurality of digital codes corresponding to respective samples of the electrical signal generated using the sensor (606). This could include operating the ADC to generate sigma-delta modulated, pulse-code modulated, or otherwise modulated string of binary bits (i.e., digital codes) related to the electrical signal. Generating digital codes (606) could include generating digital codes having binary values that correspond to ranges of values of the physiological property, e.g., such that a particular digital code having a first binary value corresponds to the physiological property having a value within a first range and the particular digital code having a second binary value corresponds to the physiological property having a value within a second range that does not substantially overlap with the first range. In some examples, the generated digital codes could be related to a change or difference between the value of the physiological property during a current sample and the value of the physiological property during a previous sample.

The method 600 includes recording, by the controller, the generated plurality of digital codes (608). This could include operating elements of a volatile memory, a plurality of volatile registers of a controller, a nonvolatile memory, a flash memory, or some other memory to record the digital codes. In some examples, recording the digital codes (608) could include determining a checksum or some other error-correction information and additionally recording such information. In some examples, recording the digital codes (608) could additionally include recording an absolute or relative timing of the digital codes in a memory.

The method 600 additionally includes determining, by the controller, that a trigger condition is met (610). Trigger conditions could include a variety of detected or determined states, e.g., a timing, a request, a user input, or some other factors, considerations, or other conditions. For example, determining that a trigger condition is met (610) could include the body-mountable device receiving a request to determine and/or provide an indication of one or more values of the physiological property. For example, a user could operate a user interface (e.g., a touch sensor, a button, a capacitive touchscreen) to request an indication of the value of the physiological property, and in response the body-mountable device could determine a value of the physiological property based on the most recently generated and recorded digital code and the calibration data. In another example, the body-mountable device could receive a request (e.g., by receiving information wirelessly using an antenna)

for values of the physiological property from an external system and could responsively determine one or more values of the physiological property based on corresponding one or more recorded digital codes and the calibration data. In some examples, the trigger condition could include receiving a supply of energy from an external source (e.g., RF energy transmitted form an external device, solar energy, thermal and/or mechanical energy scavenged from a body to which the body-mountable device is mounted).

The method 600 additionally includes determining, by the controller responsive to determining that the trigger condition is met, at least one value of the physiological property based on at least one recorded digital code and the calibration data (612). This could include adding, subtracting, multiplying, dividing, exponentiating, performing a lookup in a lookup table, or performing some other determination based on an offset, a gain, one or more polynomial coefficients, a lookup table, a threshold, or some other information of the calibration data. Determining at least one value of the physiological property (612) could include determining a single value of the physiological property, e.g., based on a most recently generated digital code of the stored plurality of digital codes. Determining at least one value of the physiological property (612) could include determining a plurality of values of the physiological property, e.g., determining a value of the physiological property for each of the generated and stored digital codes.

The method 600 could include additional steps. For example, the method 600 could include determining a health state, a course of treatment, a dose and/or timing of administration of a drug, or some other information based on a generated digital code and/or a value of the physiological property determined therefrom. The method 600 could include indicating detected analyte data, determined dosing and/or timing of administration of a drug, or some other information generated by and/or available to the device using a user interface of the device (e.g., LEDs, displays, vibrators) and/or via a user interface of an external device in communication with the device. The method 600 could include communicating (e.g., wirelessly transmitting) one or more of the generated and stored digital codes and/or one or more values of the physiological property determined therefrom. Additional and/or alternative steps, or alternative embodiments of the listed steps, are anticipated.

Figure 7:
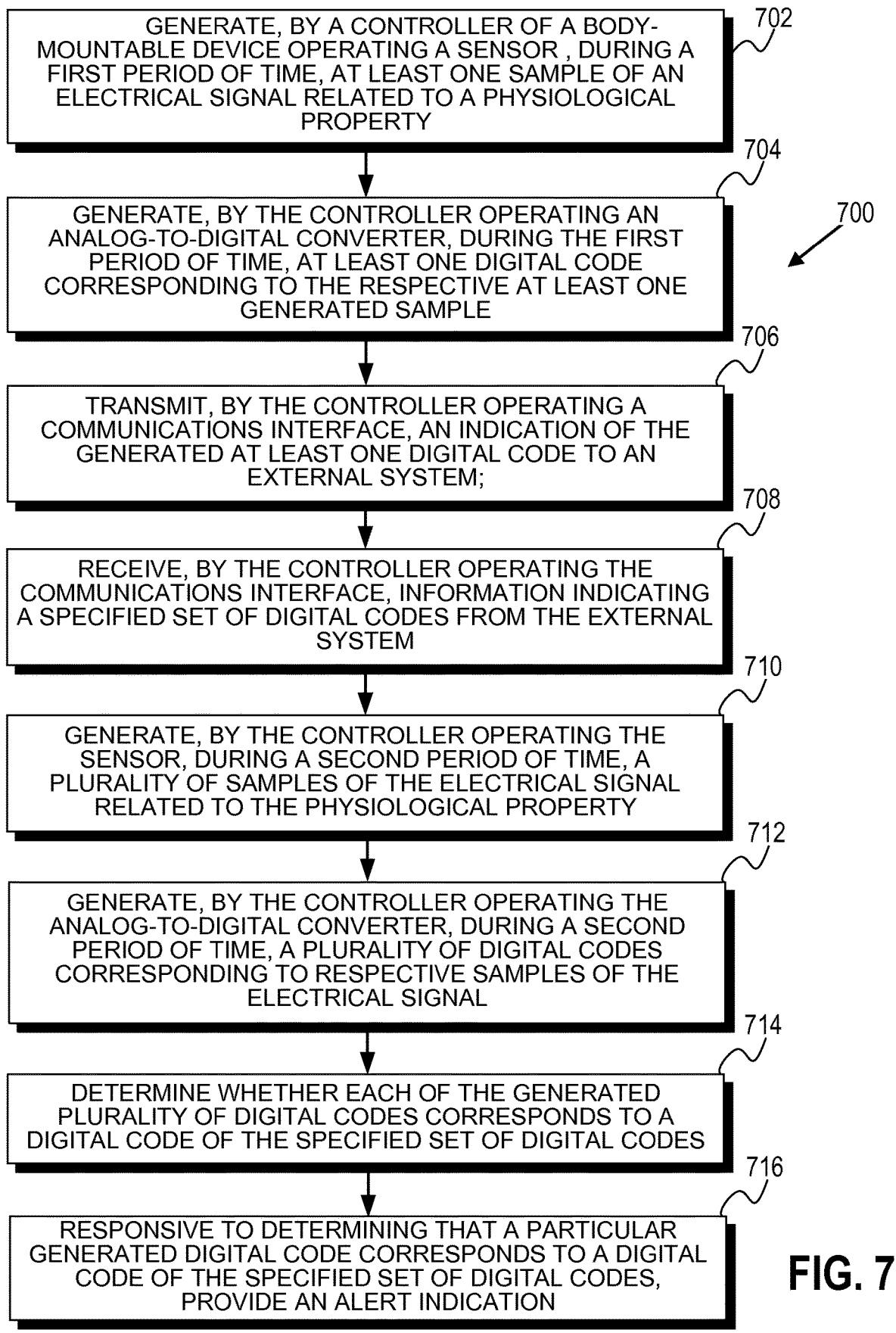
FIG. 7 is a flowchart of an example process for operating a body-mountable device.

FIG. 7 is a flowchart of a method 700 for operating a body-mountable device to detect a physiological property (e.g., a concentration of an analyte in a fluid) of a body. The body-mountable device includes (i) a flexible substrate configured to be mounted to a skin surface, (ii) a sensor that is configured to generate an electrical signal that is related to the physiological property, (iv) an analog-to-digital converter (ADC) that is configured to receive the generated electrical signal and to generate digital codes related to the received electrical signal, wherein the analog-to-digital converter is disposed on the flexible substrate, (v) a communications interface disposed on the flexible substrate, and (vi) a controller that is disposed on the substrate and that is operably coupled to the ADC and the communications interface. Operating the body-mountable device to detect a physiological property includes the controller performing the illustrated steps of the method.

The method 700 includes operating the sensor, during a first period of time, to generate at least one sample of the electrical signal related to the physiological property (702). This could include applying a voltage and/or current to electrodes of an electrochemical sensor (e.g., to a reference and/or working electrode of an electrochemical analyte sensor). Generating at least one sample of the electrical signal (702) could include operating a light detector and/or light emitter to generate samples of an electrical signal relating to an optical property of an analyte-sensitive substance having such an optical property that is related to the physiological property.

The method 700 includes operating the ADC, during the first period of time, to generate at least one digital code corresponding to the respective at least one sample of the electrical signal generated using the sensor (704). This could include operating the ADC to generate sigma-delta modulated, pulse-code modulated, or otherwise modulated string of binary bits (i.e., digital codes) related to the electrical signal. Generating at least one digital code (704) could include generating a digital code having a binary value that corresponds to a range of values of the physiological property, e.g., such that a particular digital code having a first binary value corresponds to the physiological property having a value within a first range and the particular digital code having a second binary value corresponds to the physiological property having a value within a second range that does not substantially overlap with the first range.

The method 700 includes transmitting, using the communications interface, an indication of the generated at least one digital code to an external system (706). This could include transmitting a radio frequency indication related to the at least one digital code (e.g., an amplitude-modulated, phase- or frequency-shift keyed, or otherwise modulated radio frequency transmission). This (706) could include providing an indication over a wire or other physically connected communications medium. This (706) could include transmitting an indication optically, e.g., by emitting a pattern of pulses of optical or infrared illumination to the external system.

The method 700 includes receiving, using the communications interface, information indicating a specified set of digital codes from the external system (708). This could include receiving a radio frequency signal, an optical signal, or some other wireless signal. Additionally or alternatively, this (708) could include receiving an indication via a wired or otherwise physically connected communication medium. The information indicating a specified set of digital codes could include a listing or other indication of each of the digital codes of the specified set of digital codes. Additionally or alternatively, the information indicating a specified set of digital codes could include one or more thresholds or other information indicating a range or set of digital codes (e.g., a threshold indicating that all digital codes having binary values above the threshold are part of the specified set of digital codes). The specified digital codes could include digital codes that correspond to an adverse health state (e.g., a high blood glucose level) or that correspond to some other state of interest of a body having a physiological property detected by the body-mountable device.

The method 700 includes operating the sensor, during a second period of time, to generate at least one sample of the electrical signal related to the physiological property (710). This could include applying a voltage and/or current to electrodes of an electrochemical sensor (e.g., to a reference and/or working electrode of an electrochemical analyte sensor). Generating at least one sample of the electrical signal (710) could include operating a light detector and/or light emitter to generate samples of an electrical signal relating to an optical property of an analyte-sensitive substance having such an optical property that is related to the physiological property. Generating a plurality of samples of the electrical signal (710) could include generating the electrical signal continuously across the plurality of samples (e.g., maintaining a current through electrodes of an electrochemical sensor during a period of time that includes the timing/time periods of the plurality of samples). Alternatively, generating a plurality of samples of the electrical signal (710) could include intermittently operating the sensor and/or other elements of the body-mountable device (e.g., operating a light emitter and a transimpedance amplifier that is connected to alight detector to generate a signal related to an optical property of an analyte-sensitive substance during a plurality of time periods corresponding to the plurality of samples.

The method 700 includes operating the ADC, during the second period of time, to generate a plurality of digital codes corresponding to respective samples of the electrical signal generated using the sensor (712). This could include operating the ADC to generate sigma-delta modulated, pulse-code modulated, or otherwise modulated string of binary bits (i.e., digital codes) related to the electrical signal. Generating digital codes (712) could include generating digital codes having binary values that correspond to ranges of values of the physiological property, e.g., such that a particular digital code having a first binary value corresponds to the physiological property having a value within a first range and the particular digital code having a second binary value corresponds to the physiological property having a value within a second range that does not substantially overlap with the first range. In some examples, the generated digital codes could be related to a change or difference between the value of the physiological property during a current sample and the value of the physiological property during a previous sample. In some examples, the generated digital codes could be related to a change or difference between the value of the physiological property during a current sample and the value of the physiological property during a previous sample (e.g., the ADC could be an integrating or differentiating ADC).

The method 700 includes determining whether each of the generated plurality of digital codes corresponds to a digital code of the specified set of digital codes (714). In some examples, this could include comparing each digital code to one or more thresholds indicting the specified set of digital codes (e.g., determining whether the binary value of a particular generated digital code exceeds an indicated threshold). In some examples, this (714) could include comparing each digital code to each digital code of the specified set of digital codes, e.g., using a logical comparator or other electronic component(s). Other methods of determining whether each of the generated plurality of digital codes corresponds to a digital code of the specified set of digital codes (714) are anticipated.

The method 700 includes, responsive to determining that a particular generated digital code corresponds to a digital code of the specified set of digital codes, providing an alert indication (716). This could include operating the communications interface to transmit such an indication (e.g., wirelessly, via a wire or optical fiber). Additionally or alternatively, providing an alert indication (716) could include operating a display, buzzer, or other user-interface element(s) of the communications interface to provide a user-detectable alert indication. An alert indication could simply provide an indication that an alert state has been detected (i.e., that a generated digital code matched one or more of the digital codes of the specified set of digital codes). Additionally or alternatively, an alert indication could include an indication of the generated digital code, an indication of which digital code of the set of specified digital codes matches the generated digital code, an indication of a value of the physiological property determined based on the generated digital code, or some other information. Providing an alert indication (716) could include other steps or features according to an application.

The method 700 could include additional steps. For example, the method 700 could include determining one or more values of the physiological property based on corresponding stored digital codes. The method 700 could include indicating detected analyte data, determined dosing and/or timing of administration of a drug, or some other information generated by and/or available to the device using a user interface of the device (e.g., LEDs, displays, vibrators) and/or via a user interface of an external device in communication with the device. The method 700 could include communicating (e.g., wirelessly transmitting) one or more of the generated and stored digital codes and/or one or more values of the physiological property determined therefrom. Additional and/or alternative steps, or alternative embodiments of the listed steps, are anticipated.

The methods described herein (e.g., 600, 700) could include mounting a body-mountable device to a skin surface. This could include using an adhesive layer of the body-mountable device to mount the flexible substrate to the skin surface. Additionally or alternatively, a liquid adhesive, tape, strap, dry adhesive, or other means could be used to mount the flexible substrate to the skin surface. Further, mounting a body-mountable device to a skin surface could include installing a sensor probe of the body-mountable device in the skin such that the sensor probe penetrates the skin and further such that a sensor disposed on the sensor probe is placed in contact with a fluid (e.g., interstitial fluid) within the skin. This could include placing the sensor probe in a puncture, cut, or other incision that has already been formed in the skin (e.g., by a needle, a lancet, a scalpel, or by some other means). Alternatively, the sensor probe could be configured to penetrate and/or pierce the skin (e.g., by being sharpened and/or having a sufficiently high rigidity). In some examples, mounting a body-mountable device to a skin surface could include using some sort of insertion device or insertion aid to emplace the sensor probe in the skin. In some examples, this could include coupling the sensor probe to a needle (e.g., placing the sensor probe in the channel of a half-needle) and piercing skin using the needle such that the needle and the coupled sensor probe penetrate the skin.

VI. CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A body-mountable device comprising:
a single substrate, wherein the single substrate is configured to be mounted on or within a human body;
a sensor that is disposed on the single substrate and that is configured to generate an electrical signal, wherein the electrical signal is related to a physiological property;
an analog-to-digital converter that is disposed on the single substrate, wherein the analog-to-digital converter is configured to receive the electrical signal generated by the sensor and to generate digital codes related to the received electrical signal;
a memory that is disposed on the single substrate; and
one or more processors that are disposed on the single substrate and that are operably coupled to the analog-to-digital converter and the memory, wherein the one or more processors are configured to perform controller operations comprising:
obtaining calibration data;
operating the sensor to generate a plurality of samples of the electrical signal related to the physiological property;
operating the analog-to-digital converter, during a first period of time that is subsequent to obtaining the calibration data, to generate a plurality of digital codes corresponding to respective samples of the electrical signal generated by the sensor;
recording the generated plurality of digital codes in the memory;
determining, subsequent to the first period of time, that a trigger condition is met, wherein determining that a trigger condition is met comprises at least one of: (i) receiving a user input, or (ii) receiving radio frequency energy to power the body-mountable device; and
responsive to determining that the trigger condition is met, using the calibration data to convert at least one digital code recorded in the memory into a value of the physiological property.

2. The body-mountable device of claim 1, further comprising:
a sensor probe, wherein an end of the sensor probe is configured to extend beneath the skin surface to contact interstitial fluid, and wherein the electrical signal generated by the sensor is related to an analyte in the interstitial fluid.

3. The body-mountable device of claim 2, further comprising a flexible battery, wherein the flexible battery is configured to supply power to the one or more processors.

4. The body-mountable device of claim 1, wherein the sensor comprises an electrochemical sensor.

5. The body-mountable device of claim 1, further comprising a user interface, wherein determining that a trigger condition is met comprises receiving the user input via the user interface, and wherein the controller operations further comprise using the user interface to provide an indication related to the determined at least one value of the physiological property responsive to determining that the trigger condition is met.

6. The body-mountable device of claim 1, further comprising a user interface, wherein obtaining calibration data comprises:
using the user interface to receive an additional input; and
determining the calibration data based on the additional input.

7. The body-mountable device of claim 1, further comprising an antenna, wherein determining that a trigger condition is met comprises receiving the radio frequency energy from an external system via the antenna, and wherein the controller operations further comprise using the antenna to provide an indication related to the determined at least one value of the physiological property to the external system responsive to determining that the trigger condition is met.

8. The body-mountable device of claim 1, further comprising an antenna, wherein determining that a trigger condition is met comprises receiving the radio frequency energy to power the body-mountable device via the antenna.

9. The body-mountable device of claim 1, further comprising an antenna, wherein obtaining calibration data comprises:
using the antenna to receive a communication from an external system; and
determining the calibration data based on the received communication.

10. The body-mountable device of claim 1, wherein the body-mountable device uses less than approximately 1 microwatt of power when operating the analog-to-digital converter to generate the plurality of digital codes corresponding to respective samples of the electrical signal generated by the sensor.

11. A method comprising:
operating a body-mountable device, wherein the body-mountable device comprises:
a single substrate, wherein the single substrate is configured to be mounted on or within a human body;
a sensor that is disposed on the single substrate and that is configured to generate an electrical signal, wherein the electrical signal is related to a physiological property;
an analog-to-digital converter that is disposed on the single substrate, wherein the analog-to-digital converter is configured to receive the electrical signal generated by the sensor and to generate digital codes related to the received electrical signal;

a memory that is disposed on the single substrate; and one or more processors that are disposed on the single substrate and that are operably coupled to the analog-to-digital converter and the memory; wherein the operating comprises:

obtaining, by the one or more processors, calibration data;

generating, by the one or more processors operating the sensor, a plurality of samples of the electrical signal related to the physiological property;

generating, by the one or more processors operating the analog-to-digital converter during a first period of time that is subsequent to obtaining the calibration data, a plurality of digital codes corresponding to respective samples of the electrical signal generated using the sensor;

recording, by the one or more processors, the generated plurality of digital codes in the memory;

determining, by the one or more processors subsequent to the first period of time, that a trigger condition is met, wherein determining that a trigger condition is met comprises at least one of: (i) receiving a user input, or (ii) receiving radio frequency energy to power the body-mountable device; and using the calibration data, by the one or more processors responsive to determining that the trigger condition is met, to convert at least one digital code recorded in the memory into a value of the physiological property.

12. The method of claim 11, wherein the sensor of the body-mountable device comprises an electrochemical sensor.

13. The method of claim 11, wherein the body-mountable device further comprises:

a sensor probe, wherein a second end of the sensor probe is configured to extend beneath the skin surface to contact interstitial fluid, and wherein the electrical signal generated by the sensor is related to an analyte in the interstitial fluid.

14. The method of claim 11, wherein the body-mountable device further comprises a user interface, wherein determining that a trigger condition is met comprises receiving, by the one or more processors, the user input via the user interface, and wherein the operating further comprises: providing, by the one or more processors using the user interface responsive to determining that the trigger condition is met, an indication related to the determined at least one value of the physiological property.

15. The method of claim 14, wherein obtaining calibration data comprises:

receiving, by the one or more processors using the user interface, an additional input; and determining, by the one or more processors, the calibration data based on the additional input.

16. The method of claim 11, wherein the body-mountable device further comprises an antenna, and wherein determining that a trigger condition is met comprises receiving, by the one or more processors, the radio frequency energy from an external system via the antenna, and wherein the operating further comprises: providing, by the one or more processors using the antenna responsive to determining that the trigger condition is met, an indication related to the determined at least one value of the physiological property to the external system.

17. The method of claim 11, wherein the body-mountable device further comprises an antenna, wherein determining that a trigger condition is met comprises receiving the radio frequency energy to power the body-mountable device via the antenna.

18. The method of claim 14, wherein the body-mountable device further comprises an antenna, and wherein obtaining calibration data comprises: receiving, by the one or more processors using the antenna, a communication from an external system; and determining, by the one or more processors, the calibration data based on the received communication.

19. The method of claim 11, wherein the calibration data comprise first calibration data corresponding to the operation of the body-mountable device at a first point in time and second calibration data corresponding to the operation of the body-mountable device at a second point in time, and wherein determining at least one value of the physiological property based on at least one recorded digital code and the calibration data comprises determining the at least one value of the physiological property based on a relative timing between the first and second points in time and a timing of generation of the at least one recorded digital code.

* * * * *